United States Patent
Tatebayashi

(10) Patent No.: US 10,168,852 B2
(45) Date of Patent: Jan. 1, 2019

(54) MAGNETIC RESONANCE IMAGING APPARATUS

(75) Inventor: Isao Tatebayashi, Utsunomiya (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1265 days.

(21) Appl. No.: 13/015,997

(22) Filed: Jan. 28, 2011

(65) Prior Publication Data

US 2011/0191715 A1   Aug. 4, 2011

(30) Foreign Application Priority Data

Jan. 29, 2010   (JP) .................................. 2010-019576
Dec. 13, 2010   (JP) .................................. 2010-276916

(51) Int. Cl.
*G06F 3/048* (2013.01)
*G06F 3/041* (2006.01)

(52) U.S. Cl.
CPC ............ *G06F 3/048* (2013.01); *G06F 3/0412* (2013.01)

(58) Field of Classification Search
CPC ........................... G06F 3/0412; G02F 1/13338
USPC ........................................................ 715/810
See application file for complete search history.

(56) References Cited

U.S. PATENT DOCUMENTS

| | | | | |
|---|---|---|---|---|
| 6,484,048 | B1 * | 11/2002 | Hoshino ............ | G01R 33/4833 345/419 |
| 7,081,750 | B1 * | 7/2006 | Zhang ........................... | 324/309 |
| 2003/0088173 | A1 * | 5/2003 | Kassai ................... | G01R 33/28 600/408 |
| 2004/0150668 | A1 * | 8/2004 | Myers et al. .................. | 345/771 |
| 2006/0251300 | A1 * | 11/2006 | Borgert et al. ............... | 382/128 |
| 2009/0300540 | A1 * | 12/2009 | Russell .......................... | 715/783 |
| 2011/0235070 | A1 * | 9/2011 | Otomaru ............... | G06F 3/1205 358/1.9 |

FOREIGN PATENT DOCUMENTS

| | | |
|---|---|---|
| JP | 2001-340317 | 12/2001 |
| JP | 2003-190119 | 7/2003 |
| JP | 2006-255189 | 9/2006 |
| JP | 2009-148463 | 7/2009 |

OTHER PUBLICATIONS

U.S. Appl. No. 13/004,454, Naoyuki Furudate, filed Jan. 11, 2011.
Office Action dated Apr. 10, 2014 in JP 2010-276916 with English translation.

* cited by examiner

*Primary Examiner* — Jennifer N To
*Assistant Examiner* — Ashley M Fortino
(74) *Attorney, Agent, or Firm* — Nixon & Vanderhye P.C.

(57) ABSTRACT

In the case where a main image taking process and a preliminary image taking process are contained in mutually the same series, an MRI apparatus displays list-view information showing a plurality of image taking processes contained in the series, together with an editing screen used for editing image taking conditions for one of the plurality of image taking processes, on a single screen. Further, when a selecting operation to select one of the plurality of image taking processes out of the list-view information has been received, the MRI apparatus switches the display of the editing screen that is currently being displayed on the single screen to a display of an editing screen used for editing image taking conditions for the one of the image taking processes that has been selected.

20 Claims, 15 Drawing Sheets

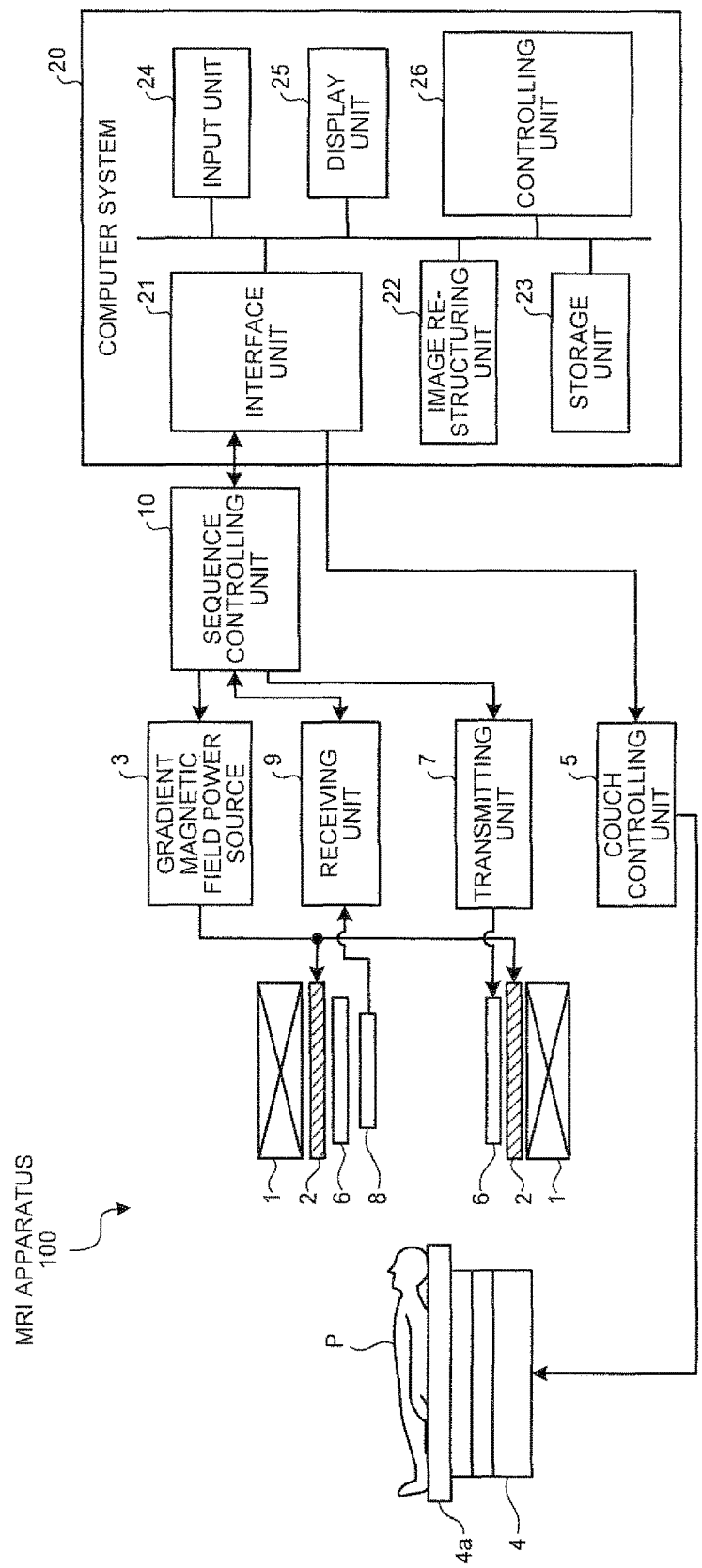

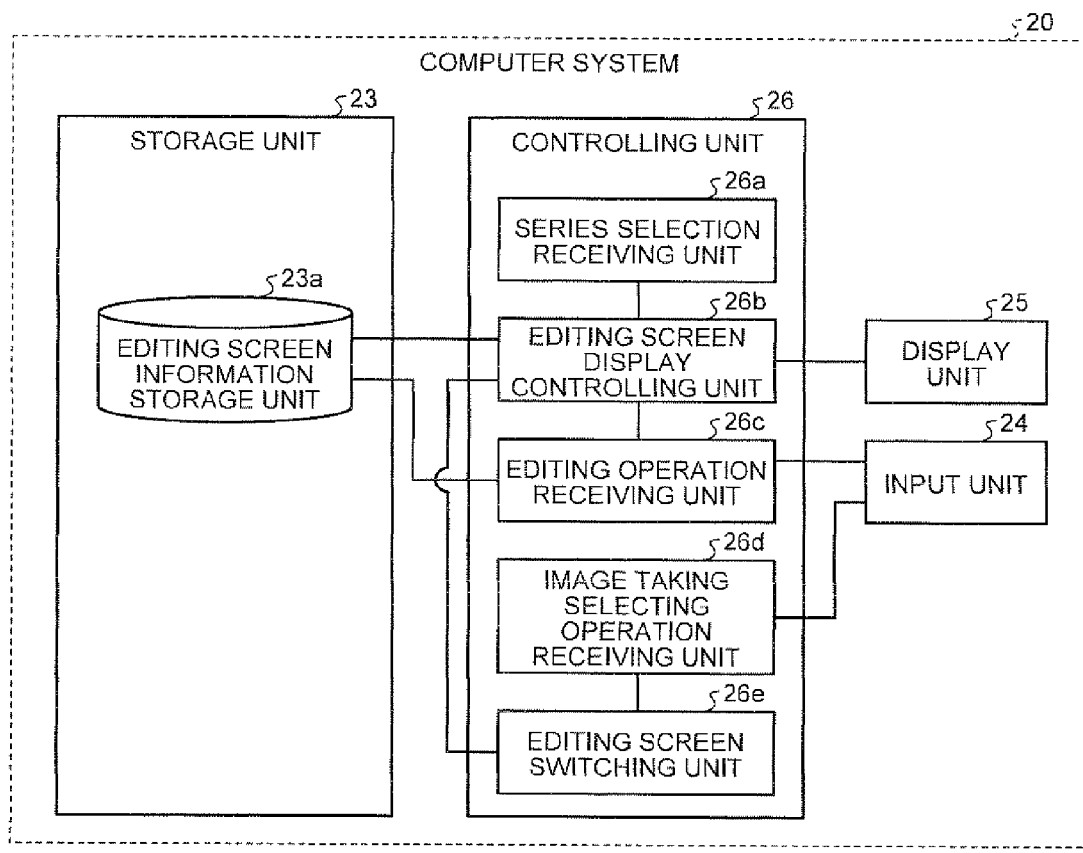

| Plane | AX_Obl/HL ▷ | A.Voice Scan int. | Off ▷ | Spatial Presat. | NONE ▷ |
| Max Slice /Cover | 128 ◁▷ | Visual Prep | Off ▷ On Off ▷ | Preset Flip Ang | ◁▷ |
| Acq. Order | Forward ▷ | SPEEDER | NONE ▷ | Skip Presat. | ▽ |
| Inter leaving | Interleave ▷ | AFI Mode | NONE ▷ | MTC Pulse | 0 ◁▷ |
| Flow Comp. | Off ▷ | Encode Order | ▽ | RF Spoiling | On ▷ |

FE_sit

FIG.6

| Plane | AX_Obl/HL | A.Voice Scan int. | Off | Spatial Presat. | NONE |
| Max Slice /Cover | 128 | Visual Prep | On | Presat Flip Ang | |
| Acq. Order | Forward | SPEEDER | NONE | Skip Presat | |
| Inter leaving | Interleave | AFI Mode | NONE | MTC Pulse | 0 |
| Flow Comp. | Off | Encode Order | | RF Spoiling | On |

FE_slt / Prep

FIG.7

| No | Scan ID |
|---|---|
| 100 | Locator |
| 200 | CHEST |
| 300 | ABDOMEN |
| 400 | LOWER ABDOMEN |
| | |
| | |
| | |
| | |
| | |

MAGNETIC RESONANCE IMAGING APPARATUS

CROSS-REFERENCE TO RELATED APPLICATIONS

This application is based upon and claims the benefit of priority from Japanese Patent Application No. 2010-19576, filed on Jan. 29, 2010; and Japanese Patent Application No. 2010-276916, filed on Dec. 13, 2010, the entire contents of which are incorporated herein by reference.

FIELD

Embodiments described herein relate generally to a medical image diagnostic apparatus.

BACKGROUND

Generally speaking, image taking processes realized by medical image diagnostic apparatuses are performed according to image taking conditions that are set in advance. For example, when an operator of a medical image diagnostic apparatus makes a plan to take images, he/she edits image taking conditions while looking at an image taking condition editing screen (hereinafter, "editing screen") that is displayed on a display unit of the medical image diagnostic apparatus. As a result, the image taking conditions that have been edited are configured into the medical image diagnostic apparatus so that the medical image diagnostic apparatus performs an image taking process according to the image taking conditions that have been configured therein. JP-A No. 2006-255189 (KOKAI) discloses an editing screen for an image taking process performed by a Magnetic Resonance Imaging (MRI) apparatus.

With regard to image taking processes performed by medical image diagnostic apparatuses, there are some situations where a plurality of image taking processes are contained in the same series. In this situation, the term "series" refers to a unit of image taking process that is performed according to a certain set of image taking conditions. Typically, "one series" corresponds to "one image taking process"; however, in some situations, a plurality of image taking processes may be contained in the same series (e.g., a main image taking process and a preliminary image taking process may be contained in one series). In this situation, the "main image taking process" refers to an image taking process that is performed so as to obtain one or more images for the main purpose (e.g., an image taking process that is performed so as to obtain one or more images used for making a diagnosis). In contrast, the "preliminary image taking process" refers to an image taking process that is performed prior to the main image taking process, for the purpose of determining parameters included in the image taking conditions for the main image taking process.

In that situation, the operator edits the image taking conditions while, for example, alternately switching the displays between an editing screen for the main image taking process and an editing screen for the preliminary image taking process. For example, while looking at the editing screen for the main image taking process, the operator performs an operation (e.g., presses a button that is displayed in a position next to a parameter related to the preliminary image taking process) to activate the editing screen for the preliminary image taking process. As a result, the editing screen for the preliminary image taking process is displayed on the display unit, replacing the editing screen for the main image taking process. When the operator needs to edit the image taking conditions for the main image taking process again, the operator further performs another operation (e.g., selects the corresponding image taking process from a menu) to activate the editing screen for the main image taking process.

The conventional technique described above, however, has a problem where there is a large burden on the operator. In other words, as explained above, in the case where a plurality of image taking processes are contained in the same series, the operator needs to, for example, edit the image taking conditions while switching between the editing screen for the main image taking process and the editing screen for the preliminary image taking process. Thus, the operations are complicated and cumbersome.

Further, the problem described above applies not only to the situation where a plurality of image taking processes are contained in the same series, but also to a situation where a plurality of series have relevance to one another. For example, to take an image of the entire body of an examined subject, because image taking processes performed by MRI apparatuses have a restriction related to uniformity of the magnetic fields, the image taking process may be, for example, divided into a plurality of series such as a series for the chest, a series for the abdomen, and a series for the lower abdomen. In that situation, the plurality of series may have relevance to one another requiring that the same image taking conditions should be set for the series or the plurality of series may have relevance to one another requiring that, intentionally, different image taking conditions should be set for the series. For this reason, the operator needs to edit the image taking conditions while switching the displays between the editing screens for the different series. The operations in this situation are also complicated and cumbersome.

BRIEF DESCRIPTION OF THE DRAWINGS

FIG. 1 is a block diagram of an MRI apparatus 100 according to a first embodiment;

FIG. 2 is a block diagram of a computer system 20 according to the first embodiment;

FIG. 3 is a drawing for explaining an example of a series list according to the first embodiment;

FIG. 4 is a drawing for explaining an example of an editing screen according to the first embodiment;

FIG. 5 is a drawing for explaining another example of the editing screen according to the first embodiment;

FIG. 6 is a drawing for explaining yet another example of the editing screen according to the first embodiment;

FIG. 7 is a drawing for explaining yet another example of the editing screen according to the first embodiment;

DETAILED DESCRIPTION

Figure 8:
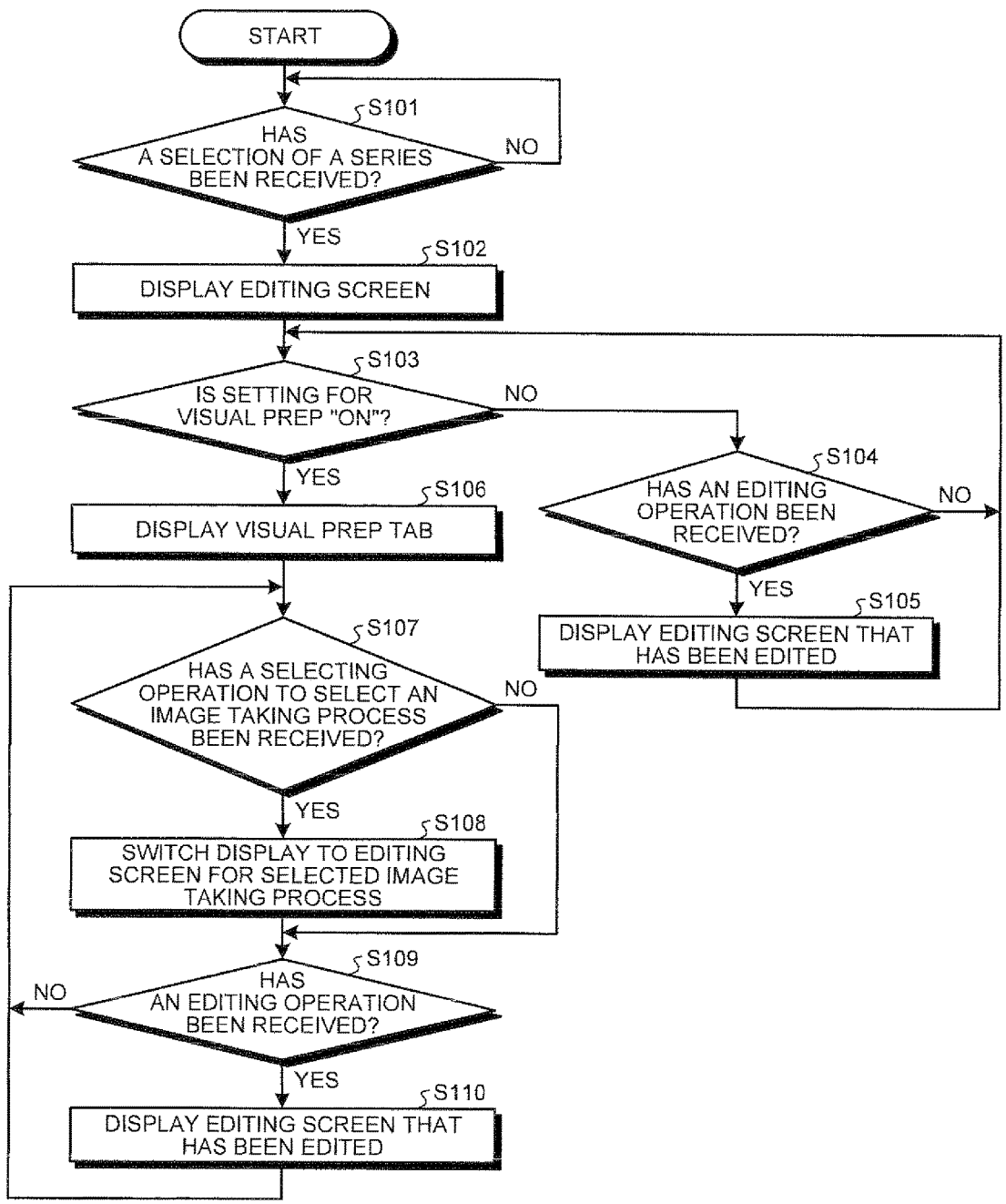
FIG. 8 is a flowchart of a processing procedure performed by the MRI apparatus 100 according to the first embodiment.

A medical image diagnostic apparatus according to the present embodiments includes a display unit and a switching unit. In the case where a plurality of series have relevance to one another, the display unit displays list-view information showing the plurality of series having the relevance to one another, together with an editing screen used for editing image taking conditions for one of the plurality of series, on a single screen. When a selecting operation to select one of the plurality of series out of the list-view information being displayed by the display unit has been received, the switching unit switches a display of the editing screen that is currently being displayed on the single screen to a display of an editing screen used for editing an image taking condition for the one of the series that has been selected.

In the following sections, exemplary embodiments of a medical image diagnostic apparatus will be explained in details. The present embodiment is not limited to the exemplary embodiments described below.

An MRI apparatus 100 according to a first embodiment will be explained, with reference to FIG. 1. FIG. 1 is a block diagram of the MRI apparatus 100 according to the first embodiment. As shown in FIG. 1, the MRI apparatus 100 according to the first embodiment includes, among others, a magnetostatic field magnet 1, a gradient coil 2, a gradient magnetic field power source 3, a couch 4, a couch controlling unit 5, a transmission coil 6, a transmitting unit 7, a reception coil 8, a receiving unit 9, a sequence controlling unit 10, and a computer system 20.

The magnetostatic field magnet 1 is formed in the shape of a hollow circular cylinder and generates a uniform magnetostatic field in the space on the inside thereof. The magnetostatic field magnet 1 may be, for example, a permanent magnet, a superconductive magnet, or the like. The gradient coil 2 is formed in the shape of a hollow circular cylinder and generates a gradient magnetic field in the space on the inside thereof. More specifically, the gradient coil 2 is disposed on the inside of the magnetostatic field magnet 1 and generates gradient magnetic fields that are in a slice direction, a phase encoding direction, and a frequency encoding direction, respectively, while receiving a supply of electric current from the gradient magnetic field power source 3. The gradient magnetic field power source 3 supplies the electric current to the gradient coil 2 according to pulse sequence execution data that has been sent from the sequence controlling unit 10.

The couch 4 includes a couchtop 4a on which an examined subject P is placed. While the examined subject P is placed thereon, the couchtop 4a is inserted into the hollow (i.e., an image taking opening) of the gradient coil 2. Normally, the couch 4 is provided so that the longitudinal direction thereof extends parallel to the central axis of the magnetostatic field magnet 1. The couch controlling unit 5 drives the couch 4 so that the couchtop 4a moves in the longitudinal direction and in an up-and-down direction.

The transmission coil 6 generates a high-frequency magnetic field. More specifically, the transmission coil 6 is disposed on the inside of the gradient coil 2 and generates the high-frequency magnetic field by receiving a supply of a high-frequency pulse from the transmitting unit 7. The transmitting unit 7 transmits the high-frequency pulse corresponding to a Larmor frequency to the transmission coil 6, according to the pulse sequence execution data that has been sent from the sequence controlling unit 10.

The reception coil 8 receives an MRI echo signal. More specifically, the reception coil 8 is disposed on the inside of the gradient coil 2 and receives the MRI echo signal emitted from the examined subject P due to an influence of the high-frequency magnetic field. Further, the reception coil 8 outputs the received MRI echo signal to the receiving unit 9. For example, the reception coil 8 may be a reception coil for the head of the examined subject, a reception coil for the spine of the examined subject, or a reception coil for the abdomen of the examined subject.

The receiving unit 9 generates MRI echo signal data based on the MRI echo signal that has been output from the reception coil 8, according to the pulse sequence execution data that has been sent from the sequence controlling unit 10. More specifically, the receiving unit 9 generates the MRI echo signal data by digitally converting the MRI echo signal that has been output from the reception coil 8 and transmits the generated MRI echo signal data to the computer system 20 via the sequence controlling unit 10.

The sequence controlling unit 10 controls the gradient magnetic field power source 3, the transmitting unit 7, and the receiving unit 9. More specifically, the sequence controlling unit 10 transmits the pulse sequence execution data that has been transmitted from the computer system 20 to the gradient magnetic field power source 3, to the transmitting unit 7, and to the receiving unit 9.

The computer system 20 includes, among others, an interface unit 21, an image restructuring unit 22, a storage unit 23, an input unit 24, a display unit 25, and a controlling unit 26. The interface unit 21 is connected to the sequence controlling unit 10 and controls inputs and outputs of data that is transmitted and received between the sequence controlling unit 10 and the computer system 20. The image restructuring unit 22 restructures image data from the MRI echo signal data that has been transmitted from the sequence controlling unit 10 and stores the restructured image data into the storage unit 23.

The storage unit 23 stores therein the image data that has been stored therein by the image restructuring unit 22 as well as other data that is used by the MRI apparatus 100. For example, the storage unit 23 may be configured by using a semiconductor memory element such as a Random Access Memory (RAM), a Read Only Memory (ROM), or a flash memory, or by using a hard disk, an optical disk, or the like.

The input unit 24 receives, for example, an operation to edit image taking conditions from the operator. For example, the input unit 24 may be a pointing device such as a mouse and/or a trackball, or a selecting device such as a mode changing switch, or an input device such as a keyboard. The display unit 25 displays image data, an editing screen, and the like. The display unit 25 is, for example, a display device such as a liquid crystal display monitor.

The controlling unit 26 controls the MRI apparatus 100 in an overall manner, by controlling the functional elements described above. For example, the controlling unit 26 may be an integrated circuit such as an Application Specific Integrated Circuit (ASIC) or a Field Programmable Gate Array (FPGA) or an electronic circuit such as a Central Processing Unit (CPU) or a Micro Processing Unit (MPU).

The MRI apparatus 100 according to the first embodiment is configured so as to, in the case where a main image taking process and a preliminary image taking process are contained in the same series, display list-view information showing a plurality of image taking processes, together with an editing screen, on a single screen. Further, when having received a selecting operation to select one of the image taking processes, the MRI apparatus 100 switches the display of the editing screen that is currently being displayed on the single screen to a display of an editing screen used for editing image taking conditions for the one of the image taking processes that has been selected. According to the first embodiment, the function of the MRI apparatus 100 described here is mainly realized by the computer system 20. Thus, in the following sections, the computer system 20 according to the first embodiment will be explained in detail.

FIG. 2 is a block diagram of the computer system 20 according to the first embodiment. As shown in FIG. 2, the storage unit 23 according to the first embodiment includes, among others, an editing screen information storage unit 23a. The editing screen information storage unit 23a stores therein various types of information that are required by processes performed by an editing screen display controlling unit 26b explained later, as well as by the preliminary image taking process and the main image taking process, the various types of information including definition information of the editing screens, preset information for the image taking conditions, and setting information of the image taking conditions that have been edited. Further, the controlling unit 26 according to the first embodiment includes, among others, a series selection receiving unit 26a, the editing screen display controlling unit 26b, an editing operation receiving unit 26c, an image taking selecting operation receiving unit 26d, and an editing screen switching unit 26e.

The series selection receiving unit 26a is configured so as to receive a selection of a series for which the image taking conditions are to be edited. More specifically, the series selection receiving unit 26a displays a list showing different series (hereinafter, the "series list") on the display unit 25 and, when a selection of one of the series has been received, notifies the editing screen display controlling unit 26b of the received information. FIG. 3 is a drawing for explaining an example of the series list according to the first embodiment. For instance, as shown in FIG. 3, the series selection receiving unit 26a obtains a series list for a corresponding medical examination from, for example, an external storage device storing therein one or more series lists and displays the obtained series list on the display unit 25 so as to receive a selection of a series out of the series list. In the example shown in FIG. 3, it is indicated that the series of which the serial number is "2000" and of which the identification information is "Field Echo FE_slt with Visual Prep" has been selected. The identification information displayed in the series list may be any information as long as it is possible to identify the series by using the information. The identification information does not necessarily have to be the same information as the identification information written on a tab, which is explained later. Further, the identification information displayed in the series list does not necessarily have to be information that includes the identification information written on a tab, either.

Next, the first embodiment will be explained by using a contrast Magnetic Resonance Angiography (MRA) process as an example in which a main image taking process and a preliminary image taking process are contained in the same series. In the following sections, the first embodiment will be explained on an assumption that the series identified by the identification information "FE_slt with Visual Prep" is a contrast MRA series and contains a main image taking process identified by identification information "FE_slt" and a preliminary image taking process identified by identification information "Prep".

During an image taking process called "contrast MRA", a contrast agent having a longitudinal relaxation time ($T_1$) shortening effect is rapidly injected into the examined subject, so that the MRI apparatus takes an image of the blood vessels into which the contrast agent has been put. In this situation, the image taking period in the contrast MRA process is in the range approximately from a number of seconds to tens of seconds. Thus, normally, one injection of a contrast agent allows an image taking process to be performed only once. Further, the contrast agent is injected from a location that is positioned away from a region (hereinafter, the "target region") that is the target of the image taking process. For this reason, the time at which it is possible to obtain an image having a good contrast after the contrast agent has reached the target region is later than the time at which the contrast agent is injected. In addition, because the delay period (i.e., how much later the former time is than the latter time) depends on the heart beat rate, the blood pressure, and the flow rate of the bloodstreams of the examined subject, the delay period is not fixed. Under these circumstances, to perform a contrast MRA process, it is important to appropriately set image taking timing. Thus, the preliminary image taking process is performed prior to the main image taking process.

There are various methods for performing the preliminary image taking process. For example, during the preliminary image taking process, the MRI apparatus 100 according to the first embodiment sequentially obtains MRI echo signals from a monitor region that is positioned close to the target region. Further, when the strength of the obtained MRI echo signals has increased so as to be equal to or larger than a predetermined threshold value, the MRI apparatus 100 starts the main image taking process in synchronization with that timing.

The editing screen display controlling unit 26b is configured so as to, in the case where a main image taking process and a preliminary image taking process are contained in the same series, display the list-view information showing a plurality of image taking processes contained in the series, together with an editing screen used for editing image taking conditions for one of the plurality of image taking processes, on a single screen. More specifically, when having received information of the series from the series selection receiving unit 26a, the editing screen display controlling unit 26b obtains a corresponding editing screen by referring to the editing screen information storage unit 23a and displays the obtained editing screen on the display unit 25.

Figure 4:
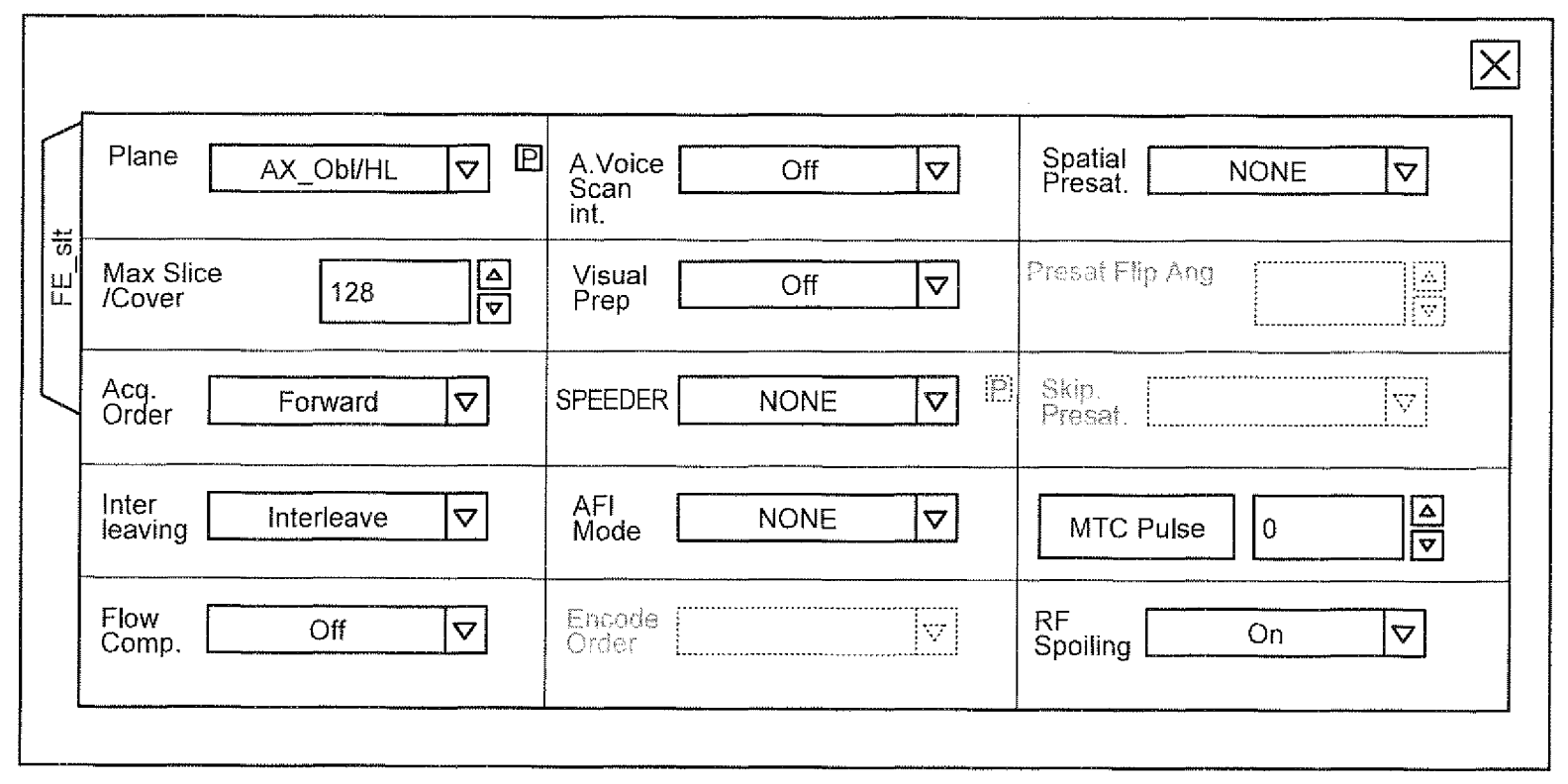

FIGS. 4 to 7 are drawings for explaining examples of the editing screen according to the first embodiment. For example, the editing screen display controlling unit 26b displays editing screens as shown in FIGS. 4 to 7. The editing screens shown in FIGS. 4 to 7 indicate transitions of the editing screens caused by receiving of operations performed by the operator.

First, according to the first embodiment, the editing screen display controlling unit 26b displays, for example, the editing screen shown in FIG. 4 on the display unit 25. The outer frame is the outline of one window that is displayed on the display unit 25. The "X" on the upper right corner is an icon used for receiving an operation to close the window. In the window, the editing screen display controlling unit 26b displays an editing screen to which tabs are attached.

According to the first embodiment, the image taking process identified by the identification information "FE_slt" is the main image taking process. Thus, first, as an editing screen for the main image taking process, the editing screen display controlling unit 26b displays an editing screen that has a tab attached thereto on which the identification information "FE_slt" is written. On the editing screen, operation tools used for setting parameters included in the image taking conditions are arranged.

The operation tools that are displayed on the editing screen are operation tools used for editing the image taking conditions for the main image taking process. It should be noted, however, that all the operation tools do not necessarily have to be displayed. An arrangement is acceptable in which only arbitrary one or more of the operation tools that are selected in advance are displayed. For example, an arrangement is acceptable in which only an operation tool that corresponds to an image taking condition having a higher possibility of being edited by the operator among a large number of image taking conditions is selected in advance and displayed in an appropriate positional arrangement on the editing screen. Further, another arrangement is acceptable in which, for example, the image taking conditions are classified in a hierarchical manner so as to be able to reduce the amount of information displayed at a time and so that the operation tools are displayed when a hierarchy button is pressed as necessary. In other words, how the positions of the operation tools are arranged and how the operation tools are displayed on the editing screen are arbitrary. The same applies to an editing screen used for the preliminary image taking process that is described later and other editing screens according to other exemplary embodiments that are described later.

According to the first embodiment, the "preliminary image taking process" refers to an image taking process that is performed prior to the main image taking process, for the purpose of determining the parameters included in the image taking conditions for the main image taking process. On the editing screen shown in FIG. 4 also, an operation tool used for setting the parameter "Visual Prep" that is included in the image taking conditions for the main image taking process is displayed.

Let us assume that the operator performs an operation to change the setting of the parameter "Visual Prep" from "Off" "On", while looking at the editing screen shown in FIG. 4. This is an operation to select performing a preliminary image taking process. For example, as shown in FIG. 5, the operator opens a pull-down menu and clicks on "On" by using a mouse. As a result, for example, as shown in FIG. 6, the setting of the parameter "Visual Prep" is changed from "Off" to "On".

According to the first embodiment, the image taking process identified by the identification information "Prep" is the preliminary image taking process. Thus, as shown in FIG. 6, the editing screen display controlling unit 26b displays an editing screen that has attached thereto not only the tab on which the identification information "FE_slt" is written, but also a tab on which the identification information "Prep" is written. In other words, as the list-view information showing the plurality of image taking processes contained in the series, the editing screen display controlling unit 26b displays the tabs. Further, like in FIGS. 4 and 5, on the editing screen, the operation tools used for setting the parameters included in the image taking conditions for the main image taking process are arranged. In other words, the editing screen display controlling unit 26b displays the list-view information showing the plurality of image taking processes contained in the same series, together with the editing screen for the main image taking process, on the single screen.

Further, according to the first embodiment, to make clear which one of the plurality of image taking processes contained in the same series corresponds to the editing screen that is currently being displayed when the editing screen display controlling unit 26b displays the list-view information together with the editing screen, the editing screen display controlling unit 26b highlights the display of the corresponding one of the image taking processes. For example, as shown in FIG. 6, in the case where the editing screen that is currently being displayed is the editing screen for the main image taking process, the editing screen display controlling unit 26b displays, for instance, the tab on which the identification information "Prep" is written, in a color that has a lower luminance level, so that the display of the tab on which the identification information "FE_slt" is written is more highlighted than the display of the tab on which the identification information "Prep" is written.

Returning to the description of FIG. 2, the editing operation receiving unit 26c is configured so as to receive an operation performed on the editing screen. More specifically, when the editing operation receiving unit 26c has received, from the operator via the input unit 24, the operation performed on the editing screen that is displayed on the display unit 25 by the editing screen display controlling unit 26b, the editing operation receiving unit 26c stores the contents of the received operation into the editing screen information storage unit 23a, and also, notifies the editing screen display controlling unit 26b of the contents of the received operation. The editing screen information storage unit 23a is configured so as to store therein setting information of the image taking conditions that have been edited. The editing screen display controlling unit 26b is configured so as to display, on the editing screen, the setting information of the image taking conditions that have been edited.

The image taking selecting operation receiving unit 26d is configured so as to receive a selecting operation to select one of the plurality of image taking processes that are contained in the same series. More specifically, when the image taking selecting operation receiving unit 26d has received, from the operator via the input unit 24, a selecting operation performed on the list-view information that is displayed on the display unit 25 by the editing screen display controlling unit 26b, the image taking selecting operation receiving unit 26d notifies the editing screen switching unit 26e of the contents of the received selection. For example, when the operator has clicked, by using a mouse, on the tab on which the identification information "Prep" is written, on the editing screen shown in FIG. 6, the image taking selecting operation receiving unit 26d notifies the editing screen switching unit 26e of the contents of the selection indicating that the identification information "Prep" has been selected.

The editing screen switching unit 26e is configured so as to switch a display of an editing screen that is currently being displayed on the single screen to a display of another editing screen used for editing the image taking conditions for one of the image taking processes that has been selected. More specifically, when having received the contents of the selection from the image taking selecting operation receiving unit 26d, the editing screen switching unit 26e notifies the editing screen display controlling unit 26b that the display should be switched to the display of the editing screen used for editing the image taking conditions for one of the image taking processes that has been selected. For example, the editing screen switching unit 26e notifies the editing screen display controlling unit 26b that the display should be switched to the display of the editing screen used for editing the image taking conditions corresponding to the identification information "Prep".

Figure 7:
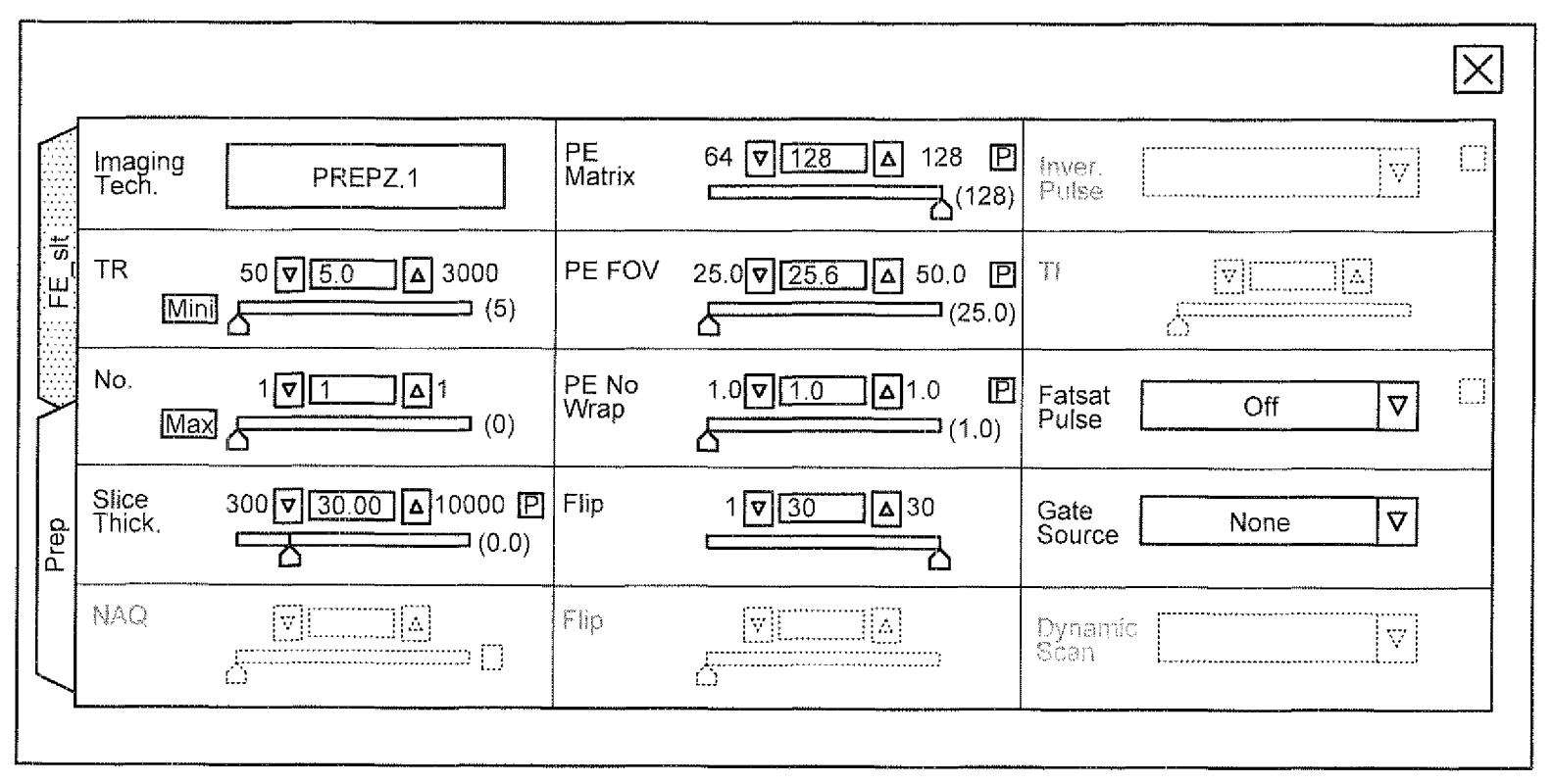

As a result, as shown in FIG. 7, for example, the editing screen display controlling unit 26b displays operation tools that are used for setting parameters included in the image taking conditions for the preliminary image taking process, unlike in the editing screen for the main image taking process shown in FIGS. 4 to 6. In other words, the editing screen display controlling unit 26b displays the list-view information showing the plurality of image taking processes contained in the same series, together with the editing screen for the preliminary image taking process, on the single screen. In this situation, the editing screen display controlling unit 26b displays, for example, the tab on which the identification information "FE_slt" is written, in a color that has a lower luminance level, so that the display of the tab on which the identification information "Prep" is written is more highlighted than the display of the tab on which the identification information "FE_slt" is written.

Next, a processing procedure performed by the MRI apparatus 100 according to the first embodiment will be explained, with reference to FIG. 8. FIG. 8 is a flowchart of the processing procedure performed by the MRI apparatus 100 according to the first embodiment.

According to the first embodiment, the series selection receiving unit 26a judges whether a selection of a series for which the image taking conditions are to be edited has been received (step S101). In the case where no selection has been received (step S101: No), the series selection receiving unit 26a returns to the process to judge whether a selection of a series for which the image taking conditions are to be edited has been received.

On the contrary, in the case where a selection has been received (step S101: Yes), the editing screen display controlling unit 26b subsequently displays an editing screen on the display unit 25 (step S102). In this situation, the editing screen display controlling unit 26b displays the editing screen for the main image taking process that has attached thereto tabs on each of which the identification information of a different one of the plurality of image taking processes contained in the same series is written.

Subsequently, the editing screen display controlling unit 26b judges whether an operation to change the setting for the parameter "Visual Prep" from "Off" to "On" has been received on the editing screen for the main image taking process (step S103).

In the case where the editing screen display controlling unit 26b has not received the operation to change the setting for the parameter "Visual Prep" to "On" (step S103: No), but the editing operation receiving unit 26c has received an editing operation performed on another parameter (step S104: Yes), the editing screen display controlling unit 26b displays, on the editing screen, setting information of the image taking conditions that have been edited (step S105) and returns to the process where the editing screen display controlling unit 26b again judges whether an operation to change the setting for the parameter "Visual Prep" from "Off" to "On" has been received.

On the contrary, in the case where the editing screen display controlling unit 26b has received an operation to change the setting for the parameter "Visual Prep" to "On" (step S103: Yes), the editing screen display controlling unit 26b displays not only the tab on which the identification information "FE_slt" is written, but also the tab on which the identification information "Prep" is written (step S106).

After that, the image taking selecting operation receiving unit 26d judges whether a selecting operation to select one of the plurality of image taking processes contained in the same series has been received (step S107). In the case where the image taking selecting operation receiving unit 26d has not received the selecting operation (step S107: No), but the editing operation receiving unit 26c has received an editing operation performed on a parameter (step S109: Yes), the editing screen display controlling unit 26b displays, on the editing screen, setting information of the image taking conditions that have been edited (step S110).

On the contrary, in the case where the image taking selecting operation receiving unit 26d has received the selecting operation (step S107: Yes), the editing screen switching unit 26e notifies the editing screen display controlling unit 26b that the display of the editing screen that is currently being displayed should be switched to a display of an editing screen used for editing the image taking conditions for the one of the image taking processes that has been selected. The editing screen display controlling unit 26b accordingly switches the display of the editing screen (step S108).

After that, in a similar manner, in the case where the editing operation receiving unit 26c has received an editing operation performed on a parameter (step S109: Yes), the editing screen display controlling unit 26b displays, on the editing screen, setting information of the image taking conditions that have been edited (step S110).

As explained above, according to the first embodiment, in the case where the main image taking process and the preliminary image taking process are contained in the same series, the editing screen display controlling unit 26b displays the list-view information showing the plurality of image taking processes contained in the series, together with the editing screen used for editing the image taking conditions for one of the image taking processes, on the single screen. Further, the image taking selecting operation receiving unit 26d receives the selecting operation to select one of the plurality of image taking processes out of the list-view information displayed by the editing screen display controlling unit 26b. Furthermore, the editing screen switching unit 26e and the editing screen display controlling unit 26b switch the display of the editing screen that is currently being displayed on the single screen to the display of the editing screen used for editing the image taking conditions for the one of the image taking processes that has been selected.

With these arrangements according to the first embodiment, the operator is able to switch between the editing screens by using the list-view information (e.g., the tabs according to the first embodiment) in a convenient manner. Thus, it is possible to reduce the burden on the operator.

In addition, according to the first embodiment, to make clear which one of the plurality of image taking processes contained in the same series corresponds to the editing screen that is currently being displayed when the editing screen display controlling unit 26b displays the list-view information together with the editing screen, the editing screen display controlling unit 26b highlights the display of the corresponding one of the image taking processes. In many situations, the editing screen for a main image taking process and the editing screen for a preliminary image taking process tend to look similar at the first sight, and it is difficult, in conventional examples, for the operator to intuitively understand which one of the image taking processes he/she is editing the image taking conditions for. In this regard, according to the first embodiment, the operator is able to visually understand which one of the image taking processes he/she is editing the image taking conditions for. Thus, also in this regard, it is possible to reduce the burden on the operator. As a result, it is also possible to reduce the mistakes that may be made by the operator during the operations.

Next, the MRI apparatus 100 according to a second embodiment will be explained. In addition to the functions that are the same as those of the MRI apparatus 100 according to the first embodiment, the MRI apparatus 100 according to the second embodiment has a function of switching between editing screens interlocked with Regions of Interest (ROIs) indicated in a locator image. In the following sections, the MRI apparatus 100 according to the second embodiment will be explained with reference to FIGS. 9 to 11.

Figure 9:
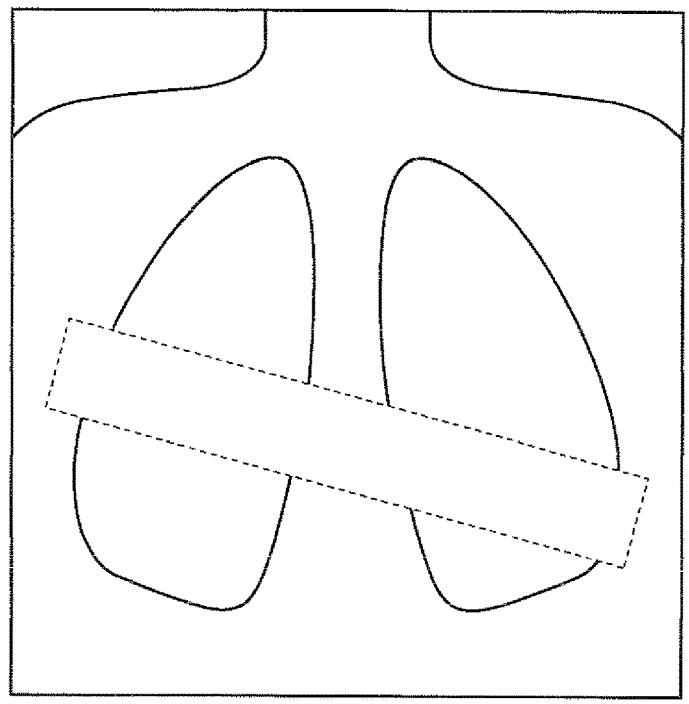
FIG. 9 is a drawing for explaining an interlocking control between an editing screen and a locator image.
Figure 10:
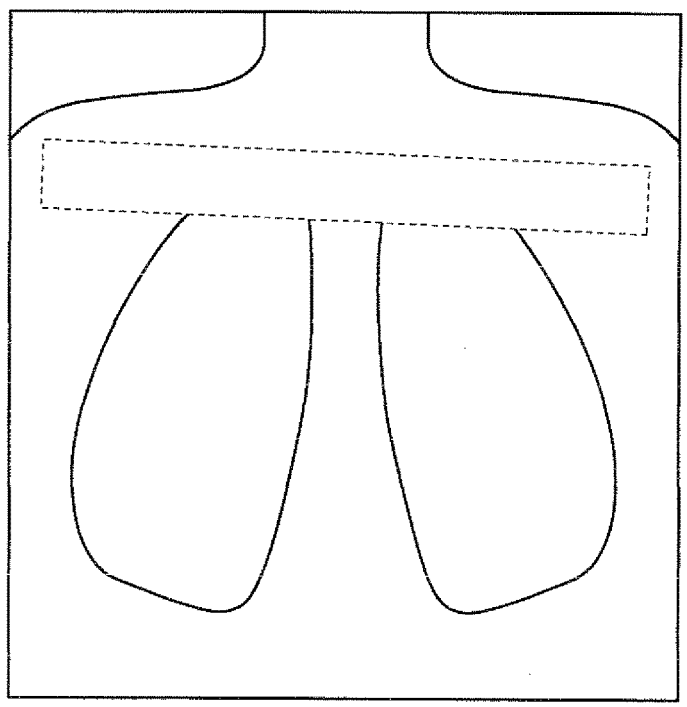
FIG. 10 is another drawing for explaining the interlocking control between an editing screen and a locator image.
Figure 11:
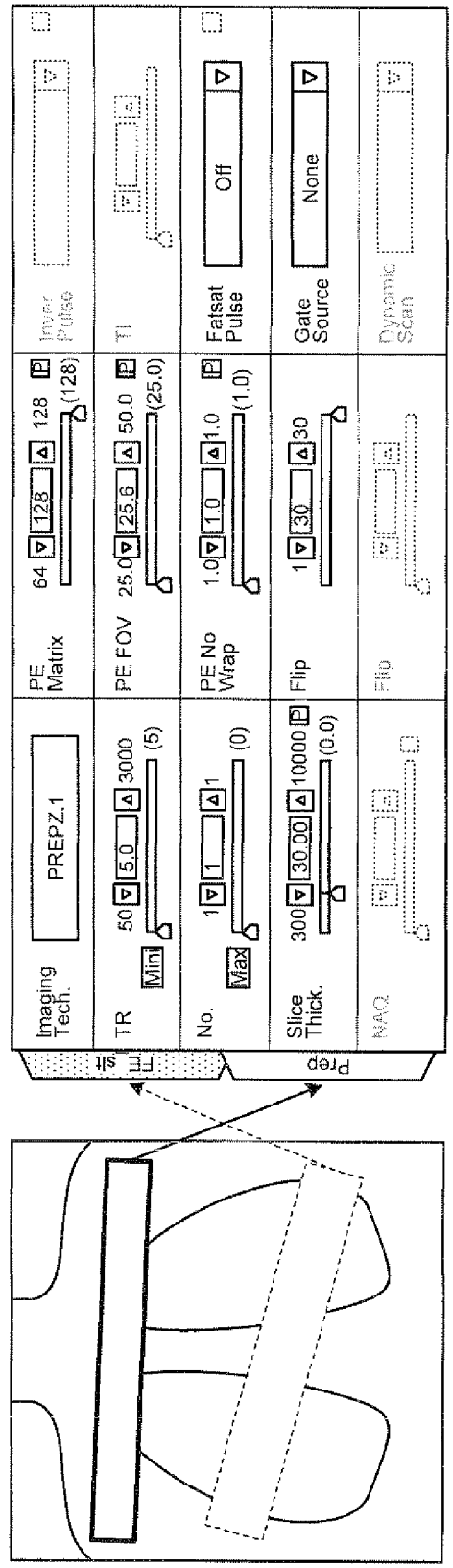
FIG. 11 is yet another drawing for explaining the interlocking control between an editing screen and a locator image.

FIGS. 9 to 11 are drawings for explaining an interlocking control between an editing screen and a locator image. In each of FIGS. 9 to 11, a ROI is indicated by a frame drawn with a dashed line. Let us assume that the ROI indicated in the locator image shown in FIG. 9 is a ROI corresponding to the main image taking process, whereas the ROI indicated in the locator image shown in FIG. 10 is a ROI corresponding to the preliminary image taking process. The locator images are one or more images that have been selected, as parent images, out of a plurality of images that had been taken in advance.

According to the second embodiment, information of the ROIs is stored in the storage unit 23. For example, the information of the ROIs is stored while being kept in correspondence with the identification information of the image taking processes. For example, the information of the ROI corresponding to the main image taking process is stored while being kept in correspondence with the image taking process identification information "FE_slt". Similarly, the information of the ROI corresponding to the preliminary image taking process is stored while being kept in correspondence with the image taking process identification information "Prep".

As an editing screen for the main image taking process, on the display unit 25, the editing screen display controlling unit 26b displays the editing screen that has attached thereto the tab on which the identification information "FE_slt" is written, and also, displays the locator image that has been collected in advance. For example, the editing screen display controlling unit 26b according to the second embodiment displays the locator image shown in FIG. 9 in a separate window.

Subsequently, as shown in FIG. 6, for example, in the case where the setting of the parameter "Visual Prep" has been changed from "Off" to "On", the editing screen display controlling unit 26b displays an editing screen that has attached thereto not only the tab on which the identification information "FE_slt" is written, but also the tab on which the identification information "Prep" is written, and also, displays the locator image as shown in FIG. 11 in a separate window.

In this situation, in the locator image shown in FIG. 11, both the ROI corresponding to the main image taking process and the ROI corresponding to the preliminary image taking process are displayed. As mentioned above, these ROIs are stored while being kept in correspondence with the identification information "FE_slt" and with the identification information "Prep", respectively. As a result, for example, when the operator has clicked, by using a mouse, on the ROI corresponding to the preliminary image taking process out of the ROIs indicated in the locator image, the image taking selecting operation receiving unit 26d notifies the editing screen switching unit 26e of the contents of the selection indicating that the ROI corresponding to the preliminary image taking process has been selected. It should be noted that, in this situation, in the example shown in FIG. 11, the display of the ROI corresponding to the preliminary image taking process, which has been selected, is more highlighted than the display of the ROI corresponding to the main image taking process. For example, the ROI corresponding to the preliminary image taking process is displayed with a solid line, whereas the ROI corresponding to the main image taking process is displayed with a dashed line.

After that, the editing screen switching unit 26e according to the second embodiment refers to the storage unit 23. Because the information of the ROI corresponding to the preliminary image taking process is stored while being kept in correspondence with the identification information "Prep", the editing screen switching unit 26e notifies the editing screen display controlling unit 26b that the display should be switched to a display of an editing screen used for editing the image taking conditions corresponding to the identification information "Prep". Accordingly, as shown in the right-hand-side portion of FIG. 11, for example, the editing screen display controlling unit 26b displays operation tools used for setting the parameters included in the image taking conditions for the preliminary image taking process.

Further, as explained above, the editing screens are configured so as to be interlocked with the ROIs that are indicated in the locator image. As a result, for example, when the operator has again clicked, by using a mouse, on the other tab on which the identification information "FE_slt" is written, the display of the ROI corresponding to the main image taking process is now highlighted.

More specifically, the image taking selecting operation receiving unit 26d notifies the editing screen switching unit 26e of the contents of the selection indicating that the identification information "FE_slt" has been selected. The editing screen switching unit 26e then notifies the editing screen display controlling unit 26b that the display should be switched to the display of the editing screen used for editing the image taking conditions corresponding to the identification information "FE_slt". As a result, the editing screen display controlling unit 26b switches the display of the editing screen that is currently being displayed on the single screen to the display of the editing screen used for editing the image taking conditions for the main image taking process, and also, highlights the display of the ROI corresponding to the main image taking process. In other words, because the information of the ROI corresponding to the main image taking process is stored while being kept in correspondence with the identification information "FE_slt", the editing screen display controlling unit 26b displays the ROI corresponding to the main image taking process with, for example, a solid line and displays the ROI corresponding to the preliminary image taking process with, for example, a dashed line, so that the display of the ROI corresponding to the main image taking process is more highlighted than the display of the ROI corresponding to the preliminary image taking process. To highlight the displays, other methods may be used. For example, it is acceptable to highlight the display by using a different luminance level.

As explained above, the ROIs and the editing screens are interlocked with one another. Thus, by selecting one of the ROIs, it is possible to switch between the editing screens. In this situation, it is also possible to highlight the display of a ROI or a tab corresponding to an editing screen that is currently being selected (i.e., so as to display the ROI or the tab in a selected state). Conversely, by selecting a tab corresponding to an editing screen, it is also possible to highlight the display of the ROI that corresponds to the editing screen that is currently being selected (i.e., so as to display the ROT in a selected state).

As explained above, according to the second embodiment, the editing screen display controlling unit 26b further displays the locator image in which the ROI has been set for each of the image taking processes contained in the series. Also, the image taking selecting operation receiving unit 26d further receives the selecting operation to select one of the plurality of ROIs out of the locator image. Further, the editing screen switching unit 26e and the editing screen display controlling unit 26b further switch the display of the editing screen that is currently being displayed on the single screen to the display of the editing screen used for editing the image taking conditions for the image taking process corresponding to the one of the ROIs that has been selected.

With these arrangements, according to the second embodiment, the switching between the editing screens is also interlocked with the ROIs that are displayed in the locator image. Thus, the operator is able to switch between the editing screens by using either the tabs or the ROIs. Consequently, the operator is able to switch between the editing screens more conveniently and more flexibly. As a result, it is possible to further reduce the burden on the operator.

In the description of the second embodiment, the example has been explained in which the editing screen that has the one tab attached thereto is kept in correspondence with the one ROI so that the one ROI is displayed in correspondence with the editing screen that has the one tab attached thereto; however, the present embodiment is not limited to this example. Another arrangement is acceptable in which a plurality of ROIs are displayed in correspondence with an editing screen that has one tab attached thereto. For example, when a multi-slab method is used, an image taking region (e.g., the spine) is divided into a plurality of slabs (i.e., a plurality of slices) so that image taking processes are performed so as to collect data from each of the slabs or the slices individually. In that situation, the one editing screen for the main image taking process is kept in correspondence with a plurality of ROIs, so that the plurality of ROIs are displayed in correspondence with the editing screen that has one tab attached thereto. As another example, an image taking process is known during which, for instance, a pre-pulse is applied to an upstream portion of an artery that traverses an image taking region, so that a marker is appended to the blood flowing into the image taking region and so that the data in the image taking region is collected when a predetermined period of time, which is set as one of the image taking conditions, has elapsed since the application of the pre-pulse. When such an image taking process that includes an application of a pre-pulse is performed, an editing screen for one image taking process is kept in correspondence with a plurality of ROIs (i.e., a ROI corresponding to the pre-pulse and another ROI corresponding to the image taking region) so that the plurality of ROIs are displayed in correspondence with the editing screen that has one tab attached thereto. This is similar in other embodiments.

In the descriptions of the first and the second embodiments, the examples have been explained in which the plurality of image taking processes are contained in the same series. However, the exemplary embodiments are not limited to these examples. It is also possible to reduce the burden on the operator even in the case where a plurality of series have relevance to one another. In the following sections, such an example will be explained as the MRI apparatus 100 according to a third embodiment For example, like in the first embodiment, the series selection receiving unit 26a according to the third embodiment obtains, based on instruction information indicating that a large-region image taking process is to be performed, a corresponding series list from, for example, an external storage device storing therein series lists and displays the obtained series list on the display unit 25. When having received a selection of one of the series, the series selection receiving unit 26a notifies the editing screen display controlling unit 26b of the received information. In this situation, the "large-region image taking process" refers to a process to take one or more images of a large region that extends over a plurality of sites of an examined subject. In that situation, for example, a method is used by which a plurality of images that partially overlap one another are taken while the couchtop on which the examined subject is placed is being moved, so that the images that have been taken are put together so as to be combined into one image. The process to put together a plurality of images so as to combine the images into one image is referred to as a "stitching process". The combined image that is obtained as a result of a stitching process is referred to as a "stitched image". Further, in the following sections, a one-time image taking process that is performed while the couchtop is being moved will be referred to as a "station".

Figures 12, 13:
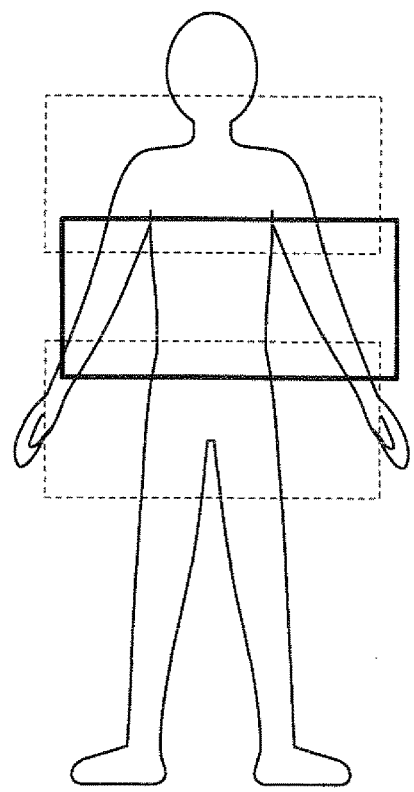
FIG. 12 is a drawing for explaining an example of a series list according to a third embodiment.
FIG. 13 is a drawing for explaining an example in which a plurality of series have relevance to one another.

FIG. 12 is a drawing for explaining an example of a series list according to the third embodiment. For example, as shown in FIG. 12, the series selection receiving unit 26a displays a series list for a large-region image taking process on the display unit 25 and receives a selection of a series out of the series list. In FIG. 12, the series "Locator" of which the serial number is "100" corresponds to an image taking process of a parent image of a locator image. Further, it is assumed that image taking processes corresponding to three stations (i.e., image taking processes for the "chest", the "abdomen", and the "lower abdomen") are performed as the large-region image taking process. The example shown in FIG. 12 indicates that three series as follows have been selected: a series of which the serial number is "200" and of which the identification information is "chest"; a series of which the serial number is "300" and of which the identification information is "abdomen"; and a series of which the serial number is "400" and of which the identification information is "lower abdomen".

FIG. 13 is a drawing for explaining an example in which a plurality of series have relevance to one another. In the description of the third embodiment, as an example in which a plurality of series have relevance to one another, an example will be explained in which, as shown in FIG. 13, the image taking processes are performed while being divided into a series for the chest, a series for the abdomen, and a series for the lower abdomen.

In that situation, the plurality of series may have relevance to one another requiring that mutually the same image taking conditions should be set for the series or the plurality of series may have relevance to one another requiring that, intentionally, different image taking conditions should be set for the series. As a result, in conventional examples, the operator needs to edit the image taking conditions while switching the displays between the editing screens corresponding to the different series, and the operations in that situation are also complicated and cumbersome. Also, in that situation, it is difficult for the operator to intuitively understand which one of the series he/she is editing the image taking conditions for.

In this regard, the editing screen display controlling unit 26b according to the third embodiment is configured so as to display list-view information showing the plurality of series that have relevance to one another, together with an editing screen used for editing the image taking conditions for one of the plurality of series, on a single screen. For example, when having received information of three series from the series selection receiving unit 26a, the editing screen display controlling unit 26b selects one of the three series e.g., the series for the abdomen), obtains an editing screen for the corresponding series by referring to the editing screen information storage unit 23a, and displays the obtained editing screen on the display unit 25.

Figure 14:
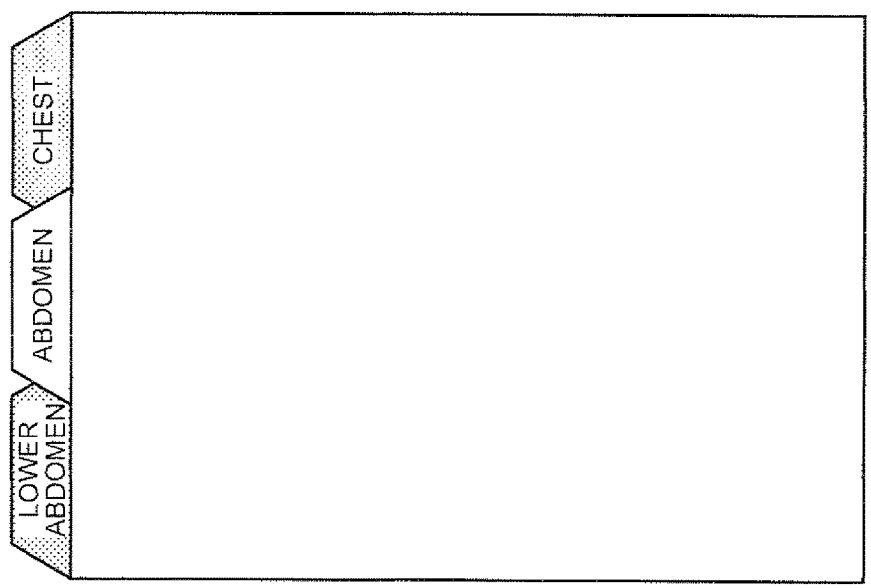
FIG. 14 is a drawing for explaining an example of an editing screen according to the third embodiment.

FIG. 14 is a drawing for explaining an example of the editing screen according to the third embodiment. As shown in FIG. 14, the editing screen display controlling unit 26b according to the third embodiment displays an editing screen that has attached thereto not only a tab on which the identification information "abdomen" is written, but also a tab on which the identification information "chest" is written and a tab on which the identification information "lower abdomen" is written. In other words, the editing screen display controlling unit 26b displays the tabs as list-view information showing the plurality of series that have relevance to one another. Further, on the editing screen, operation tools used for setting the parameters included in the image taking conditions for the series of the abdomen are arranged (not shown in FIG. 14). In other words, the editing screen display controlling unit 26b displays the list-view information showing the plurality of series that have relevance to one another, together with the editing screen for the series of the abdomen, on the single screen.

In the description above, the example has been explained in which, when the three series of the "chest", the "abdomen", and the "lower abdomen" have been selected, the tabs corresponding to these three series are displayed as the list-view information showing the plurality of series that have relevance to one another; however, the present embodiment is not limited to this example. For example, let us assume that the MRI apparatus 100 has stored in the storage unit 23 in advance information indicating that the three series of the "chest", the "abdomen", and the "lower abdomen" have relevance to one another. In that situation, for example, when one of the three series (e.g., the "abdomen") has been selected, the editing screen display controlling unit 26b refers to the storage unit 23 and displays, based on the information indicating that the three series of the "chest", "the abdomen", and the "lower abdomen" have relevance to one another, the list-view information showing all of the three series, together with an editing screen for the series of the abdomen, on the single screen.

Further, according to the third embodiment, to make clear which one of the plurality of series corresponds to the editing screen that is currently being displayed when the editing screen display controlling unit 26b displays the list-view information together with the editing screen, the editing screen display controlling unit 26b highlights the display of the corresponding one of the series. For example, as shown in FIG. 14, in the case where the editing screen that is currently being displayed is an editing screen for the series of the abdomen, the editing screen display controlling unit 26b displays, for example, the tab on which the identification information "chest" is written and the tab on which the identification information "lower abdomen" is written, in a color that has a lower luminance level, so that the display of the tab on which the identification information "abdomen" is written is more highlighted than the display of the tab on which the identification information "chest" is written and the display of the tab on which the identification information "lower abdomen" is written.

The image taking selecting operation receiving unit 26d according to the third embodiment receives a selecting operation to select one of the plurality of series. More specifically, when the image taking selecting operation receiving unit 26d has received, from the operator via the input unit 24, a selecting operation performed on the list-view information that is displayed on the display unit 25 by the editing screen display controlling unit 26b, the image taking selecting operation receiving unit 26d notifies the editing screen switching unit 26e of the contents of the received selection. For example, on the editing screen shown in FIG. 14, when the operator has clicked, by using a mouse, on the tab on which the identification information "lower abdomen" is written, the image taking selecting operation receiving unit 26d notifies the editing screen switching unit 26e of the contents of the selection indicating that the identification information "lower abdomen" has been selected.

The editing screen switching unit 26e according to the third embodiment is configured so as to switch the display of the editing screen that is currently being displayed on the single screen to a display of an editing screen used for editing the image taking conditions for one of the series that has been selected. More specifically, when the editing screen switching unit 26e has received the contents of the selection from the image taking selecting operation receiving unit 26d, the editing screen switching unit 26e notifies the editing screen display controlling unit 26b that the display should be switched to the display of the editing screen used for editing the image taking conditions for the series that has been selected. For example, the editing screen switching unit 26e notifies the editing screen display controlling unit 26b that the display should be switched to the display of the editing screen used for editing the image taking conditions corresponding to the identification information "lower abdomen".

As a result, the editing screen display controlling unit 26b according to the third embodiment displays the operation tools for setting the parameters included in the image taking conditions for the series of the lower abdomen. In other words, the editing screen display controlling unit 26b displays the list-view information showing the plurality of series that have relevance to one another, together with the editing screen for the series of the lower abdomen, on the single screen. In that situation, the editing screen display controlling unit 26b displays the tab on which the identification information "chest" is written and the tab on which the identification information "abdomen" is written in a color that has a lower luminance level, so that the display of the tab on which the identification information "lower abdomen" is written is more highlighted than the displays of the tab on which the identification information "chest" is written and the tab on which the identification information "abdomen" is written.

Figure 15:
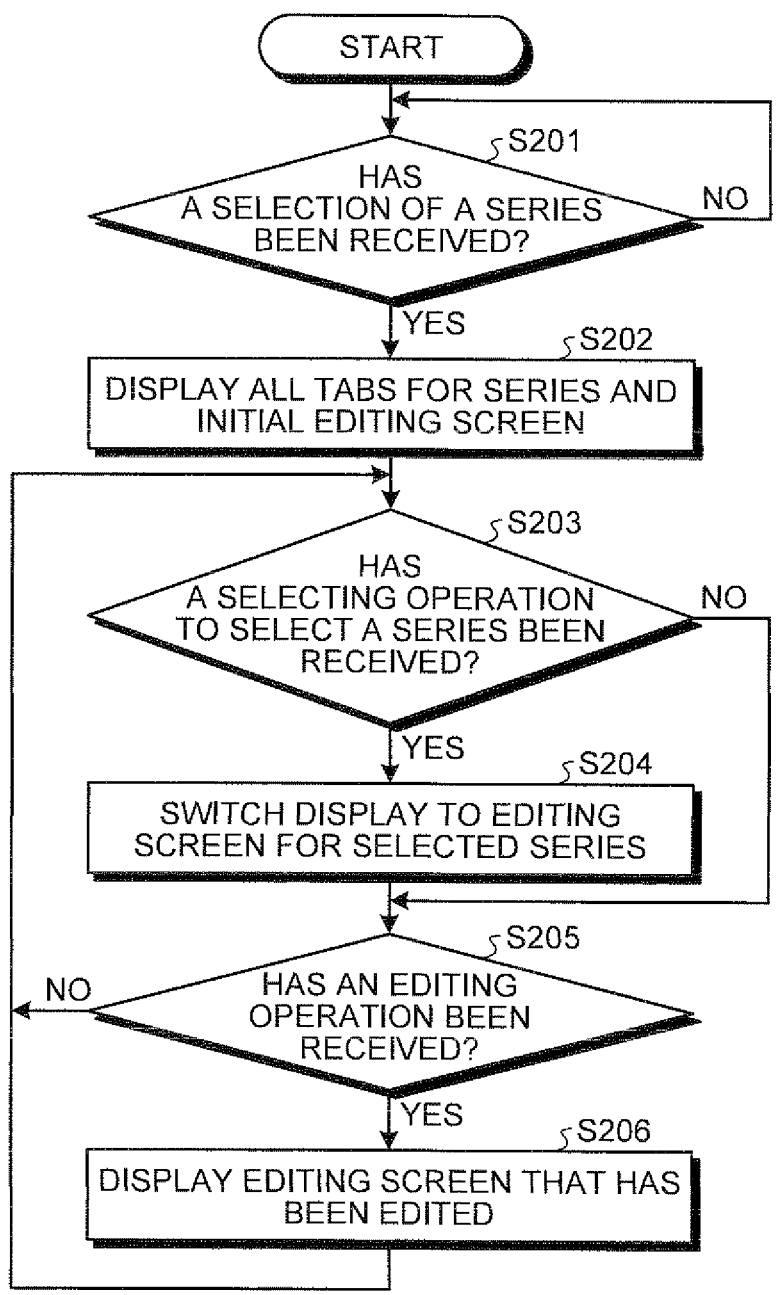
FIG. 15 is a flowchart of a processing procedure performed by the MRI apparatus 100 according to the third embodiment.

Next, a processing procedure performed by the MRI apparatus 100 according to the third embodiment will be explained, with reference to FIG. 15. FIG. 15 is a flowchart of the processing procedure performed by the MRI apparatus 100 according to the third embodiment.

According to the third embodiment, the series selection receiving unit 26a judges whether a selection of a series for which the image taking conditions are to be edited has been received (step S201). In the case where no selection has been received (step S201: No), the series selection receiving unit 26a returns to the process to judge whether a selection of a series for which the image taking conditions are to be edited has been received.

On the contrary, in the case a selection has been received (step S201: Yes), the editing screen display controlling unit 26b subsequently displays an editing screen on the display unit 25 (step S202). In this situation, the editing screen display controlling unit 26b displays an initial editing screen that has attached thereto tabs on each of which the identification information of a different one of the plurality of series that have relevance to one another is written.

Subsequently, the image taking selecting operation receiving unit 26d judges whether a selecting operation to select one of the plurality of series has been received (step S203). In the case where the image taking selecting operation receiving unit 26d has not received the selecting operation (step S203: No), but the editing operation receiving unit 26c has received an editing operation performed on a parameter (step S205: Yes), the editing screen display controlling unit 26b displays, on the editing screen, setting information of the image taking conditions that have been edited (step S206).

On the contrary, in the case where the image taking selecting operation receiving unit 26d has received the selecting operation (step S203: Yes), the editing screen switching unit 26e notifies the editing screen display controlling unit 26b that the display of the editing screen that is currently being displayed should be switched to a display of the editing screen used for editing the image taking conditions for the series that has been selected. The editing screen display controlling unit 26b accordingly switches the display of the editing screen (step S204).

After that, in a similar manner, in the case where the editing operation receiving unit 26c has received an editing operation performed on a parameter (step 205: Yes), the editing screen display controlling unit 26b displays, on the editing screen, setting information of the image taking conditions that have been edited (step S206).

As explained above, according to the third embodiment, in the case where a plurality of series have relevance to one another, the editing screen display controlling unit 26b displays the list-view information showing the plurality of series that have relevance to one another, together with the editing screen used for editing the image taking conditions for one of the series, on the single screen. Further, the image taking selecting operation receiving unit 26d receives the selecting operation to select one of the plurality of series out of the list-view information that is displayed by the editing screen display controlling unit 26b. Further, the editing screen switching unit 26e and the editing screen display controlling unit 26b switch the display of the editing screen that is currently being displayed on the single screen to the display of the editing screen used for editing the image taking conditions for the series that has been selected.

As explained above, according to the third embodiment, the operator is able to switch between the editing screens by using the list-view information (e.g., the tabs according to the third embodiment) in a convenient manner. Thus, it is possible to reduce the burden on the operator.

Further, according to the third embodiment, to make clear which one of the plurality of series corresponds to the editing screen that is currently being displayed when the editing screen display controlling unit 26b displays the list-view information together with the editing screen, the editing screen display controlling unit 26b highlights the display of the corresponding one of the series. In many situations, the editing screens for mutually different series tend to look similar at the first sight, and it is difficult, in conventional examples, for the operator to intuitively understand which one of the series he/she is editing the image taking conditions for. In this regard, according to the third embodiment, the operator is able to visually understand which one of the series he/she is editing the image taking conditions for. Thus, also in this regard, it is possible to reduce the burden on the operator. In addition, it is also possible to reduce the mistakes that may be made by the operator during the operations.

Next, the MRI apparatus 100 according to a fourth embodiment will be explained. In addition to the functions that are the same as those of the MRI apparatus 100 according to the third embodiment, the MRI apparatus 100 according to the fourth embodiment has a function of switching between editing screens interlocked with ROIs indicated in a locator image. In the following sections, the MRI apparatus 100 according to the fourth embodiment will be explained with reference to FIG. 16.

Figure 16:
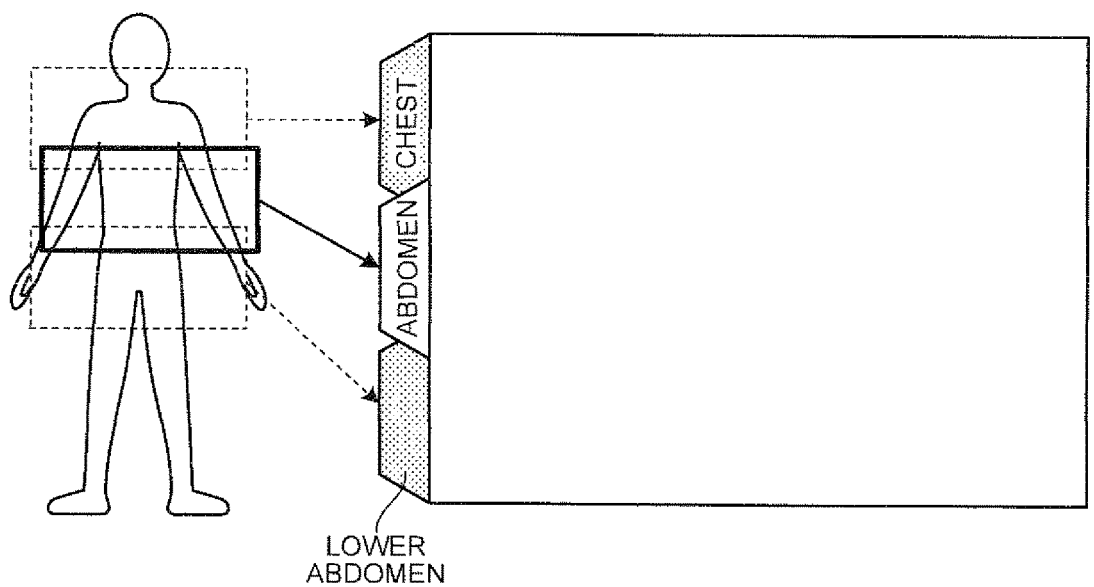
FIG. 16 is a drawing for explaining an interlocking control between an editing screen and a locator image.

FIG. 16 is a drawing for explaining an interlocking control between an editing screen and a locator image. The image of an examined subject displayed in FIG. 16 is a locator image and is a stitched image that has been obtained as a result of a stitching process. In FIG. 16, each of the ROIs is indicated by a frame drawn with a dashed line. The selected ROI is indicated by a frame drawn with a solid line. According to the fourth embodiment, the information of the ROIs are stored in the storage unit 23 and are stored, for example, while being kept in correspondence with the identification information of the series. For example, the information of the ROI in the chest is stored while being kept in correspondence with the identification information "chest" identifying the series of the chest. Also, the information of the ROI in the abdomen is stored while being kept in correspondence with the identification information "abdomen" identifying the series of the abdomen. Further, the information of the ROI in the lower abdomen is stored while being kept in correspondence with the identification information "lower abdomen" identifying the series of the lower abdomen.

For example, on the display unit 25, the editing screen display controlling unit 26b displays an editing screen that has attached thereto three tabs such as a tab on which the identification information "chest" is written, a tab on which the identification information "abdomen" is written, and a tab on which the identification information "lower abdomen" is written, and also, displays a locator image that has been collected in advance. For example, the editing screen display controlling unit 26b according to the fourth embodiment displays the locator image as shown in FIG. 16 in a separate window.

In the locator image shown in FIG. 16, the ROI in the chest, the ROI in the abdomen, and the ROI in the lower abdomen are all displayed. As explained above, the ROIs are stored while being kept in correspondence with the identification information "chest", the identification information "abdomen", and the identification information "lower abdomen", respectively. As a result, for example, when the operator has clicked, by using a mouse, on the ROI in the abdomen out of the ROIs that are indicated in the locator image, the image taking selecting operation receiving unit 26d notifies the editing screen switching unit 26e of the contents of the selection indicating that the ROI in the abdomen has been selected. It should be noted that, in this situation, in the example shown in FIG. 16, the display of the ROI in the "abdomen", which has been selected, is more highlighted than the displays of the ROIs in the "chest" and the "lower abdomen". For example, the ROI in the "abdomen" is displayed with a solid line, whereas the ROIs in the "chest" and the "lower abdomen" are each displayed with a dashed line.

After that, the editing screen switching unit 26e according to the fourth embodiment refers to the storage unit 23. Because the information of the ROI in the abdomen is stored while being kept in correspondence with the identification information "abdomen", the editing screen switching unit 26e notifies the editing screen display controlling unit 26b that the display should be switched to a display of an editing screen used for editing the image taking conditions corresponding to the identification information "abdomen". Accordingly, as shown in FIG. 16, the editing screen display controlling unit 26b displays operation tools used for setting the parameters included in the image taking conditions for the series of the abdomen.

Further, as explained above, the editing screens are configured so as to be interlocked with the ROIs that are indicated in the locator image. As a result, for example, when the operator has again clicked, by using a mouse, on another tab on which the identification information "chest" is written, the display of the ROT in the "chest" is now highlighted.

More specifically, the image taking selecting operation receiving unit 26d notifies the editing screen switching unit 26e of the contents of the selection indicating that the identification information "chest" has been selected. The editing screen switching unit 26e then notifies the editing screen display controlling unit 26b that the display should be switched to a display of the editing screen used for editing the image taking conditions corresponding to the identification information "chest". As a result, the editing screen display controlling unit 26b switches the display of the editing screen that is currently being displayed on the single screen to the display of the editing screen used for editing the image taking conditions for the series of the chest, and also, highlights the display of the ROI in the "chest". In other words, because the information of the ROI in the "chest" is stored while being kept in correspondence with the identification information "chest", the editing screen display controlling unit 26b displays the ROT in the "chest" with, for example, a solid line and displays the ROIs in the "abdomen" and the "lower abdomen" with, for example, a dashed line, so that the display of the ROI in the "chest" is more highlighted than the displays of the ROIs in the "abdomen" and the "lower abdomen". To highlight the displays, other methods may be used. For example, it is acceptable to highlight a display by using a different luminance level.

As explained above, the ROIs and the editing screens are interlocked with one another. Thus, by selecting one of the ROIs, it is possible to switch between the editing screens. In this situation, it is also possible to highlight the display of a ROI or a tab corresponding to an editing screen that is currently being selected (i.e., so as to display the ROI or the tab in a selected state). Conversely, by selecting a tab corresponding to an editing screen, it is also possible to highlight the display of the ROI that corresponds to the editing screen that is currently being selected (i.e., so as to display the ROI in a selected state).

As explained above, according to the fourth embodiment, the editing screen display controlling unit 26b further displays the locator image in which the ROI has been set for each of the series. Also, the image taking selecting operation receiving unit 26d further receives the selecting operation to select one of the plurality of ROIs out of the locator image. Further, the editing screen switching unit 26e and the editing screen display controlling unit 26b further switch the display of the editing screen that is currently being displayed on the single screen to the editing screen used for editing the image taking conditions for the series corresponding to the one of the ROIs that has been selected.

With these arrangements, according to the fourth embodiment, the switching between the editing screens is also interlocked with the ROIs that are displayed in the locator image. Thus, the operator is able to switch between the editing screens by using either the tabs or the ROIs. Consequently, the operator is able to switch between the editing screens more conveniently and more flexibly. As a result, it is possible to further reduce the burden on the operator.

Figure 17:
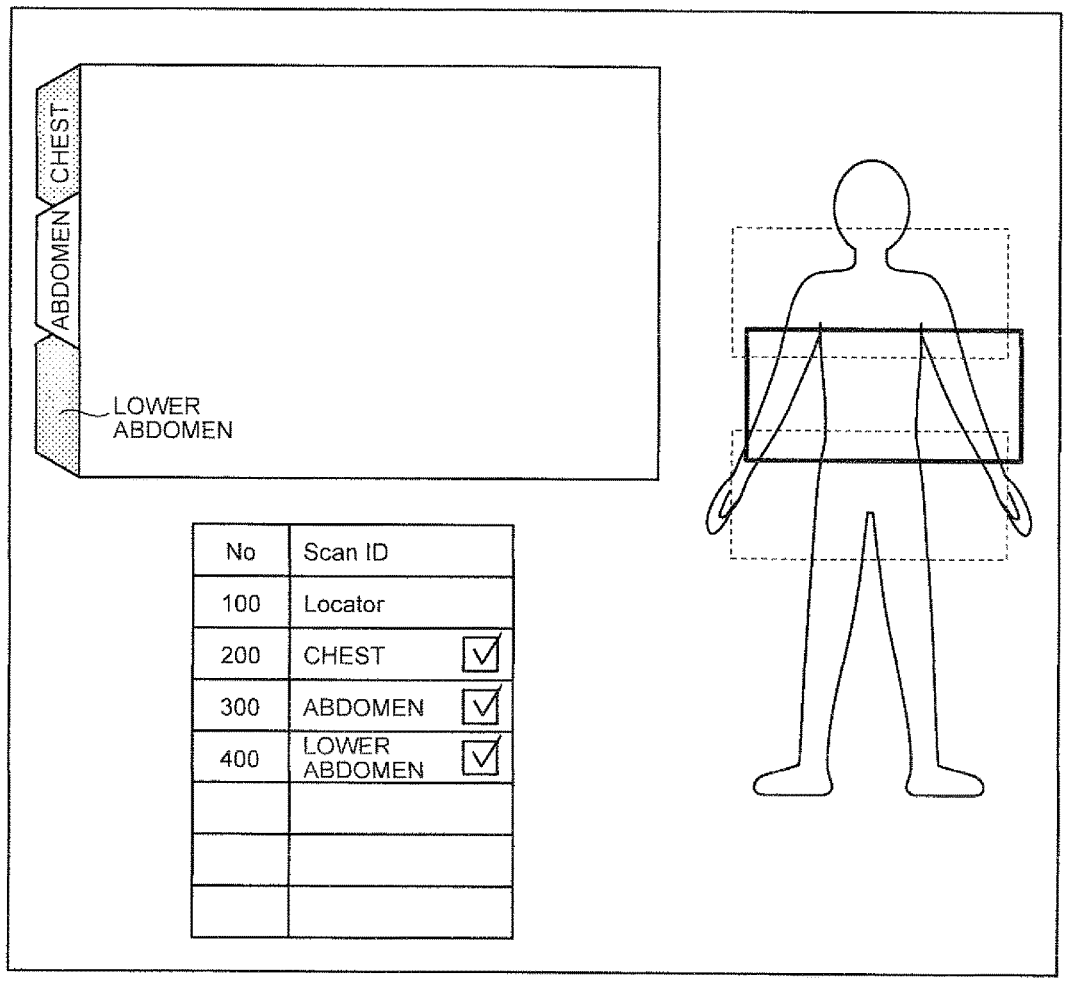
FIG. 17 is a drawing for explaining another example of an editing screen according to a fourth embodiment.
Figure 18:
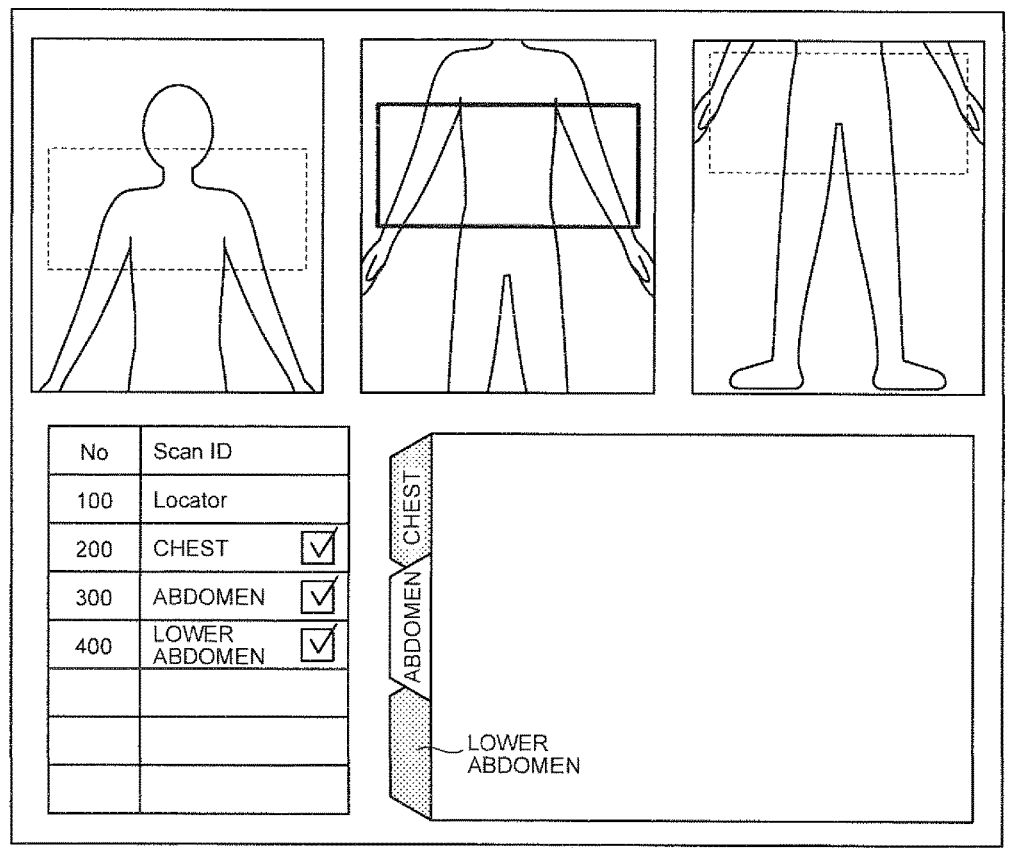
FIG. 18 is a drawing for explaining yet another example of an editing screen according to the fourth embodiment.

Further, the MRI apparatus 100 according to any of the exemplary embodiments may be configured so as to display, for example, an editing screen shown in FIG. 17 or FIG. 18, instead of the editing screen shown in FIG. 16. FIGS. 17 and 18 are drawings for explaining other examples of the editing screen according to the fourth embodiment.

For example, in the example shown in FIG. 17, the editing screen display controlling unit 26b displays, on a single screen, a series list, an editing screen itself to which tabs are attached, and a locator image in which ROIs are displayed. It should be noted that the positional arrangement shown in FIG. 17 is only an example.

In addition to the interlocking between the ROIs and the editing screens that is explained above, the editing screen display controlling unit 26b is configured so as to further realize an interlocking with the series list. In the description of the third embodiment, the example has been explained in which, when the three series such as the "chest", the "abdomen", and the "lower abdomen" have been selected, the tabs corresponding to the three series are displayed as the list-view information showing the plurality of series that have relevance to one another. In this situation, in the example shown in FIG. 17, the editing screen display controlling unit 26b dynamically changes the selection so as to dynamically change the list-view information and the ROIs that are displayed.

For example, in the example shown in FIG. 17, the selection of series is made by using check boxes. For example, let us assume that the operator has unchecked the check box corresponding to the series of the "lower abdomen". In that situation, for example, the editing screen display controlling unit 26b receives, from the series selection receiving unit 26a, information indicating that the series of the "lower abdomen" has been eliminated and arranges so that the tab of the "lower abdomen" is no longer displayed in the list-view information that is currently being displayed on the display unit 25. Further, for example, the editing screen display controlling unit 26b arranges so that the ROI in the "lower abdomen" is no longer displayed among the ROIs that are currently being displayed in the locator image.

It is possible to realize the interlocking with the series list as explained above, regardless of whether the series list is displayed on the single screen. In other words, even in the case where the series list is displayed in a separate window or the like, the editing screen display controlling unit 26b is able to dynamically change the list-view information and the ROIs that are displayed, in correspondence with dynamic changes in the selection of the series.

Further, for example, as shown in FIG. 18, the editing screen display controlling unit 26b may display the images prior to the stitching process, as locator images. It should be noted that the positional arrangement shown in FIG. 18 is only an example.

In that situation also, the editing screen display controlling unit 26b is able to configure the ROIs and the editing screens so as to be interlocked with one another. Further, the editing screen display controlling unit 26b is able to dynamically change the list-view information and the ROIs that are displayed, in correspondence with dynamic changes in the selection of the series. To highlight the display of the ROIs, other than the method by which the display of the ROTS themselves is highlighted, it is acceptable to use a method by which the display of the entirety of the one of the three locator images in which the corresponding ROI is displayed is highlighted (e.g., by changing the frame of the locator image to a bold frame or a frame having a higher luminance level). Alternatively, it is also acceptable to use these methods in combination.

Further, it is possible to materialize the present embodiment in various modes other than those described in the exemplary embodiments above.

In the description of the first and the second embodiments, the contrast MRA was used as an example in which a main image taking process and a preliminary image taking process are contained in the same series; however, the present embodiment is not limited to this example. In the following sections, other examples will be explained.

For example, the MRI apparatus according to any of the exemplary embodiments may similarly be applied to a synchronized image taking process in which the position of the diaphragm is used as a synchronization signal. For example, when an image of the heart is taken, it is desirable to keep the influence of breathing as little as possible. Thus, during the synchronized image taking process in which the position of the diaphragm is used as a synchronization signal, a region including the diaphragm is set as a ROI for a preliminary image taking process, separately from a ROI for a main image taking process. The preliminary image taking process for detecting the position of the diaphragm is performed prior to the main image taking process, so that the position of the diaphragm that has been detected during the preliminary image taking process can be used as the synchronization signal. During one series, a set that is made up of the preliminary image taking process and the main image taking process is repeatedly performed.

For example, during the preliminary image taking process, the MRI apparatus excites the ROI for the preliminary image taking process by using an exciting method that is different from the exciting method used on the ROI for the main image taking process, so as to obtain data for the purpose of detecting movements. After that, the MRI apparatus generates a signal called "navigator" from the obtained data. Further, the MRI apparatus detects the position of the diaphragm based on the navigator signal and determines what hardware controlling method should be used and whether data should be collected during the main image taking process, according to the amount of changes in the position of the diaphragm. Further, the MRI apparatus calculates an amount of movements that is required in a movement correction process performed on the data collected during the main image taking process, by multiplying the amount of movements of the diaphragm by a fixed ratio.

In that situation, for example, the MRI apparatus displays list-view information showing a preliminary image taking process to collect data from a region including the diaphragm and a main image taking process to collect data from a region including the heart, together with an editing screen used for, for example, editing image taking conditions for the preliminary image taking process, on a single screen. Further, for example, when the MRI apparatus has received a selecting operation to select the main image taking process out of the list-view information, the MRI apparatus switches the display of the editing screen that is currently being displayed on the single screen to a display of an editing screen used for editing the image taking conditions for the main image taking process, which has been selected.

Further, for example, the MRI apparatus according to any of the exemplary embodiments may similarly be applied to a cardiography synchronized image taking process. During a cardiography synchronized image taking process, a preliminary image taking process to determine synchronization timing is performed prior to a main image taking process.

For example, during the preliminary image taking process, the MRI apparatus obtains an Electrocardiogram (ECG) signal from a cardiographic testing unit that is attached to the surface of the body of an examined subject and obtains a plurality of bloodstream images while dynamically changing a delay period from a peak reaching time of an R wave. After that, a medical doctor or the like makes a visual observation of the plurality of bloodstream images and determines, for example, the most appropriate delay period for the systole and for the diastole so as to set the delay periods as parameters included in the image taking conditions for the main image taking process. With these arrangements, the MRI apparatus performs the main image taking process while using the most appropriate delay periods that have been determined during the preliminary image taking process as the synchronization timing.

In that situation, for example, the MRI apparatus displays list-view information showing the preliminary image taking process to obtain the plurality of bloodstream images and the main image taking process that is performed while using the most appropriate delay periods for the systole and for the diastole as the synchronization timing, together with an editing screen used for editing the image taking conditions for one of the plurality of image taking processes, on a single screen. Further, for example, when the MRI apparatus has received a selecting operation to select another one of the image taking processes out of the list-view information, the MRI apparatus switches the display of the editing screen that is currently being displayed on the single screen to a display of an editing screen used for editing image taking conditions for said another one of the image taking processes that has been selected.

Further, for example, the MRI apparatus according to any of the exemplary embodiments may similarly be applied to a non-contrast angiography process. Non-contrast angiography is an image taking process to obtain images of blood vessels and/or information about bloodstreams of an examined subject, without injecting a contrast agent into the examined subject. During a non-contrast angiography process, when a phenomenon called "flow void" has occurred, a problem arises where, for example, the strength of MRI echo signals to be collected become lower. For this reason, it is desirable to understand the degree of the flow void in advance and to set parameters for each examined subject, while taking the flow void into consideration. Further, for example, when an image of the blood vessels in the leg is to be taken, because the flow rate in the blood vessels is different for each person, it is desirable to collect information about the flow rate of the bloodstreams for each examined subject in advance and to set parameters for each examined subject while taking the flow rate of the bloodstreams into consideration.

For example, during a preliminary image taking process, the MRI apparatus performs the image taking process a plurality of times, while dynamically changing the values of parameters. In this situation, the parameters include, for example, the strength of a diphase pulse related to the flow void phenomenon, an effective Echo Time (TE), a flow compensation pulse, an Inversion Time (TI), an Echo Train Spacing (ETS) period, a flip angle for a fat saturation pulse (Fat Sat), a TI to be used after a fat saturation pulse (Fat Sat) has been applied, a flip angle of a Magnetization Transfer (MT) pulse, and a flip angle of a refocus pulse.

For example, the MRI apparatus obtains an ECG signal from a cardiographic testing unit that is attached to the surface of the body of an examined subject and performs, a plurality of times, a data collecting process to collect data from an image taking site of the examined subject while using the same delay period from the peak reaching time of the R-wave (i.e., in the same cardiac phase), while dynamically changing the values of the parameters. As a result, it is possible to collect and restructure image data of a plurality of images for the same image taking site. After that, a medical doctor or the like makes a visual observation of the plurality of images that have been restructured and specifies, for example, one of the images that has the highest image quality. As a result, the values of the parameters that are set for the specified image are identified, so that the identified values of the parameters can be used during the main image taking process.

In that situation, the MRI apparatus displays list-view information showing the preliminary image taking process that is performed a plurality of times while dynamically changing the values of the parameters and the main image taking process, together with an editing screen used for editing the image taking conditions for one of the plurality of image taking processes, on a single screen. Further, for example, when the MRI apparatus has received a selecting operation to select another one of the image taking processes out of the list-view information, the MRI apparatus switches the display of the editing screen that is currently being displayed on the single screen to a display of an editing screen used for editing image taking conditions for said another one of the image taking processes that has been selected.

Further, in the description of the first through the fourth embodiments, the MRI apparatus was used as an example of the medical image diagnostic apparatus according to the exemplary embodiments; however, the exemplary embodiments are not limited this example. It is possible to similarly apply the present embodiments to an X-ray Computed Tomography (CT) apparatus or a Positron Emission Tomography (PET) apparatus.

Further, in the description of the first through the fourth embodiments, the example was explained in which the editing screen corresponding to one of the image taking processes (or one of the series) is displayed as the editing screen, so that the display is switched between the editing screens according to the selecting operations; however, the exemplary embodiments are not limited to this example. For example, another arrangement is acceptable in which all the editing screens for the main image taking process and for the preliminary image taking process that are contained in mutually the same series are simultaneously displayed as editing screens to which the identification information identifying the image taking processes is attached. For example, it is acceptable to simultaneously display, on a single screen, an editing screen for the main image taking process to which a "FE_slt" tab is attached and an editing screen for the preliminary image taking process to which a "Prep" tab is attached. Further, in that situation, to make clear which one of the image taking processes corresponds to the editing screen that is currently being edited, it is acceptable to highlight the display of the corresponding one of the image taking processes. For example, while the operator is editing the editing screen for the main image taking process to which the "FE_slt" tab is attached, the "Prep" tab is displayed with a lower luminance level.

Further, in the description of the first through the fourth embodiments, the example in which the "tabs" are used as the list-view information was explained; however, the present embodiment is not limited to this example. For example, it is acceptable to use the "ROIs" as the list-view information. For example, in the examples shown in FIGS. 16 to 18, it is possible to treat the ROIs that are indicated in the locator images as the list-view information, instead of displaying the tabs as the list-view information.

When the medical image diagnostic apparatus according to an aspect of the present embodiments is used, an advantageous effect is achieved where it is possible to reduce the burden on the operator of the apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
    MRI gantry components including static and gradient magnetic field generators, at least one radio-frequency coil coupled to an imaging volume, RF transmitting and receiving circuits, at least one operator input/output device including a visual display, data storage and at least one control processor configured to control said gantry components by executing computer program instructions to effect:
    display one of a plurality of overlapping editing windows, each overlapping editing window being configured for operator-setting of concurrently displayed MRI data acquisition parameters defining a respectively corresponding one of a plurality of mutually-related different types of MR image-taking processes,
    display non-overlapped operator-selectable regions with each of the plurality of overlapped editing windows on a single display screen, the operator-selectable regions respectively corresponding to each of said MR image-taking processes,
    wherein each of said MR image-taking processes includes an MRI scan that executes an MRI pulse sequence for acquiring magnetic resonance signals, and said operator-set MRI data acquisition parameters for said different types of MR image-taking processes have inter-related relevance to one another, and wherein, when one of the non-overlapped operator-selectable regions is selected, switching from a display of one of the editing windows to a display of another one of the editing windows corresponding to another one of the MR image-taking processes is effected.

2. The magnetic resonance imaging apparatus according to claim 1, wherein to make clear which one of the plurality of MR image-taking processes corresponds to the editing window that is currently being displayed when the non-overlapped operator-selectable regions are displayed, the display of the operator-selectable region corresponding to the one of the plurality of MR image-taking processes is highlighted.

3. The magnetic resonance imaging apparatus according to claim 2, wherein the operator-selectable regions comprise tabs that are respectively associated with said MR image taking processes.

4. The magnetic resonance imaging apparatus according to claim 2, wherein the display of MRI data acquisition parameters defining a plurality of MR image-taking processes includes a concurrently displayed locator image having visible regions of interest respectively corresponding to each of the image-taking processes.

5. The magnetic resonance imaging apparatus according to claim 1, wherein
a locator image is also concurrently displayed in which a region of interest is visually present for each of the plurality of MR image-taking processes, and
wherein the control processor is further configured to effect, when an operator selection of a different region of interest on the locator image is received, switching the display of the editing window that is currently being displayed to a display of an editing window used for editing a scan condition that corresponds to the different one of the regions of interest that has been selected.

6. The magnetic resonance imaging apparatus according to claim 5, wherein the operator-selectable regions comprise displayed tabs that are respectively associated with said MR image taking processes.

7. The magnetic resonance imaging apparatus according to claim 5, wherein to make clear which one of the plurality of MR image-taking processes corresponds to the editing window that is currently being displayed, an enhanced display is made of at least one of the following: (a) the operator-selectable region corresponding to the one of the plurality of MR image-taking processes; and (b) one of the visually displayed regions of interest corresponding to the one of the plurality of MR image-taking processes.

8. The magnetic resonance imaging apparatus according to claim 1, wherein the operator-selectable regions comprise displayed tabs that are respectively associated with said MR image taking.

9. The magnetic resonance imaging apparatus according to claim 1, wherein the display of MRI data acquisition parameters defining a plurality of MR image-taking processes includes a concurrently displayed locator image having visible regions of interest respectively corresponding to each of the image-taking processes.

10. A magnetic resonance imaging (MRI) apparatus comprising:
MRI gantry components including static and gradient magnetic field generators, at least one radio-frequency coil coupled to an imaging volume, RF transmitting and receiving circuits, at least one operator input/output device including a visual display, data storage and at least one control processor configured to control said gantry components by executing computer program instructions to effect:
where a main scan and a preliminary scan that is performed prior to the main scan for a purpose of determining a MRI data acquisition parameter for the main scan are contained in a same series, display of list-view information showing a plurality of scans contained in the series together with each of a plurality of overlapped editing windows on a single display screen, each editing window being configured for operator-setting of concurrently displayed MRI data acquisition parameters defining a respectively corresponding one of the plurality of scans,
wherein the plurality of scans each executes a pulse sequence so as to acquire a magnetic resonance signal, and said operator-set MRI data acquisition parameters for said plurality of scans have relevance to one another, and
wherein when one of the scans shown in the list-view information is selected, switching from a display of said one of the editing windows currently being displayed to a display of another one of the editing windows corresponding to the selected scan is effected.

11. The magnetic resonance imaging apparatus according to claim 10, wherein to make clear which one of the plurality of scans contained in the series corresponds to the editing window that is currently being displayed when the list-view information is displayed together with the editing window, the display of the scan shown in the list-view information corresponding to the one of the plurality of scans is highlighted.

12. The magnetic resonance imaging apparatus according to claim 11, wherein the list-view information comprises non-overlapped displayed tabs that respectively associated with said plurality of scans.

13. The magnetic resonance imaging apparatus according to claim 11, wherein the list-view information is configured with a concurrently displayed locator image having visible regions of interest respectively corresponding to each of the scans in the series.

14. The magnetic resonance imaging apparatus according to claim 10, wherein
a locator image is also concurrently displayed in which a region of interest is visually present for each of the scans contained in the series, and
when an operator selection of a different region of interest on the locator image is received, the display of the editing window that is currently being displayed is switched to a display of another editing window used for editing a scan condition for a scan that corresponds to the selected different region of interest.

15. The magnetic resonance imaging apparatus according to claim 14, wherein the list-view information comprises non-overlapped displayed tabs that respectively associated with said plurality of scans.

16. The magnetic resonance imaging apparatus according to claim 14, wherein to make clear which one of the plurality of scans contained in the series corresponds to the editing window that is currently being displayed, a highlighted display is made of at least one of the following: (a) the scan shown in the list-view information corresponding to the one of the plurality of scans; and (b) one of the visually displayed regions of interest corresponding to the plurality of scans.

17. The magnetic resonance imaging apparatus according to claim 10, wherein the list-view information comprises non-overlapped displayed tabs that are respectively associated with said plurality of scans.

18. The magnetic resonance imaging apparatus according to claim 10, wherein the list-view information is configured with a concurrently displayed locator image having visible regions of interest respectively corresponding to each of the scans in the series.

19. A magnetic resonance imaging (MRI) apparatus comprising:
at least one processor with an associated memory and display configured to concurrently display (a) a subject image and (b) one of a plurality of overlapping editing windows for editing an MRI scan condition for one of a plurality of series of MRI scans, the series having relevance between scan conditions thereof and each including a scan that executes a pulse sequence for acquiring magnetic resonance signals, wherein
the subject image is displayed together with each of the plurality of overlapping editing windows on a single screen,
the subject image includes thereon a plurality of graphics each representing a different region of interest corresponding to one of the plurality of series of MRI scans, and
each of the editing windows includes thereon a parameter of a scan condition for one of the plurality of series of MRI scans and is used for editing the parameter of the scan condition; and
when a selecting operation to select one of the plurality of graphics on the subject image is received, a display of said one of the editing windows currently being displayed is switched to a display of another one of the editing windows corresponding to the selected graphic.

20. A magnetic resonance imaging apparatus comprising:
at least one processor with an associated memory and display configured to concurrently display (a) a subject image and (b) one of a plurality of overlapping editing windows for editing an MRI scan condition for one of a plurality of MRI scans included in a series, the series including a main scan and a preliminary scan that is performed prior to the main scan for a purpose of determining a parameter included in a scan condition for the main scan, the scans each executing an MRI pulse sequence for acquiring magnetic resonance signals, wherein
the subject image is displayed together with each of the plurality of overlapping editing windows on a single screen,
the subject image includes thereon a plurality of graphics each representing a different region of interest corresponding to one of the plurality of MRI scans, and
each of the editing windows includes thereon a parameter of a scan condition for one of the plurality of MRI scans, and is used for editing the parameter of the scan condition; and
when a selecting operation to select one of the plurality of graphics on the subject image is received, a display of said one of the editing windows currently being displayed is switched to a display of another one of the editing window corresponding to the selected graphic.

* * * * *